US008848865B2

(12) United States Patent
Nakayama

(10) Patent No.: US 8,848,865 B2
(45) Date of Patent: Sep. 30, 2014

(54) RADIOGRAPHIC IMAGE CAPTURING APPARATUS

(75) Inventor: Hiroki Nakayama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 13/456,884

(22) Filed: Apr. 26, 2012

(65) Prior Publication Data

US 2012/0277625 A1 Nov. 1, 2012

(30) Foreign Application Priority Data

Apr. 27, 2011 (JP) .................. 2011-099367

(51) Int. Cl.
*A61B 6/04* (2006.01)
*A61B 10/02* (2006.01)
*A61B 10/00* (2006.01)
*A61B 6/02* (2006.01)
*A61B 6/00* (2006.01)

(52) U.S. Cl.
CPC ........... *A61B 6/0414* (2013.01); *A61B 10/0041* (2013.01); *A61B 6/025* (2013.01); *A61B 6/488* (2013.01); *A61B 6/0457* (2013.01); *A61B 6/4452* (2013.01); *A61B 6/502* (2013.01); *A61B 10/0275* (2013.01); *A61B 6/022* (2013.01)
USPC ........................................... 378/37

(58) Field of Classification Search
CPC ....... A61B 6/502; A61B 6/0414; A61B 6/025
USPC ........................................... 378/37
See application file for complete search history.

(56) References Cited

U.S. PATENT DOCUMENTS

| | | | |
|---|---|---|---|
| 5,050,197 A | 9/1991 | Virta et al. | |
| 6,122,542 A | 9/2000 | Lee et al. | |
| 6,304,770 B1 | 10/2001 | Lee et al. | |
| 6,928,315 B1 | 8/2005 | Nachaliel | |
| 7,742,796 B2 | 6/2010 | Eberhard et al. | |
| 2002/0061090 A1 | 5/2002 | Lindstrom et al. | |
| 2008/0080668 A1 | 4/2008 | Kashiwagi | |
| 2008/0103387 A1 | 5/2008 | Gross | |
| 2008/0181361 A1 | 7/2008 | Eldered et al. | |
| 2009/0003519 A1* | 1/2009 | Defreitas et al. ................ | 378/37 |
| 2009/0135997 A1 | 5/2009 | Defreitas et al. | |

FOREIGN PATENT DOCUMENTS

| | | |
|---|---|---|
| JP | 54-020676 A | 2/1979 |
| JP | 54-020676 U | 2/1979 |
| JP | 03-110400 U | 11/1991 |

(Continued)

OTHER PUBLICATIONS

Communication, dated Aug. 21, 2012, issued in corresponding EP Application No. 12165678.9, 7 pages.

(Continued)

*Primary Examiner* — Courtney Thomas
(74) *Attorney, Agent, or Firm* — Sughrue Mion, PLLC

(57) ABSTRACT

A radiographic image capturing apparatus includes a compression member, which is displaceable with respect to a holding member that holds a target object to be examined. The compression member is displaced toward the holding member for compressing the target object held by the holding member while the compression member is tilted with respect to the holding member along lateral directions of the target object as viewed in front elevation.

15 Claims, 28 Drawing Sheets

(56) References Cited

FOREIGN PATENT DOCUMENTS

| | | |
|---|---|---|
| JP | 2000157554 A | 6/2000 |
| JP | 2002219124 A | 8/2002 |
| JP | 2008086451 A | 4/2008 |
| JP | 2008-513093 A | 5/2008 |
| JP | 2008513090 A | 5/2008 |
| JP | 2009082399 A | 4/2009 |
| JP | 2009-207681 A | 9/2009 |
| JP | 2009-285345 A | 12/2009 |
| JP | 2010-088586 A | 4/2010 |
| JP | 2010-158561 A | 7/2010 |
| WO | 2006/031082 A1 | 3/2006 |

OTHER PUBLICATIONS

Rejection of the Application, dated Apr. 16, 2013, issued in corresponding JP Application No. 2011-099367, 5 pages in English and Japanese.

Communication pursuant to Article 94(3) EPC, dated Dec. 12, 2013, issued in corresponding EP Application No. 12 165 678.9, 6 pages in English.

* cited by examiner

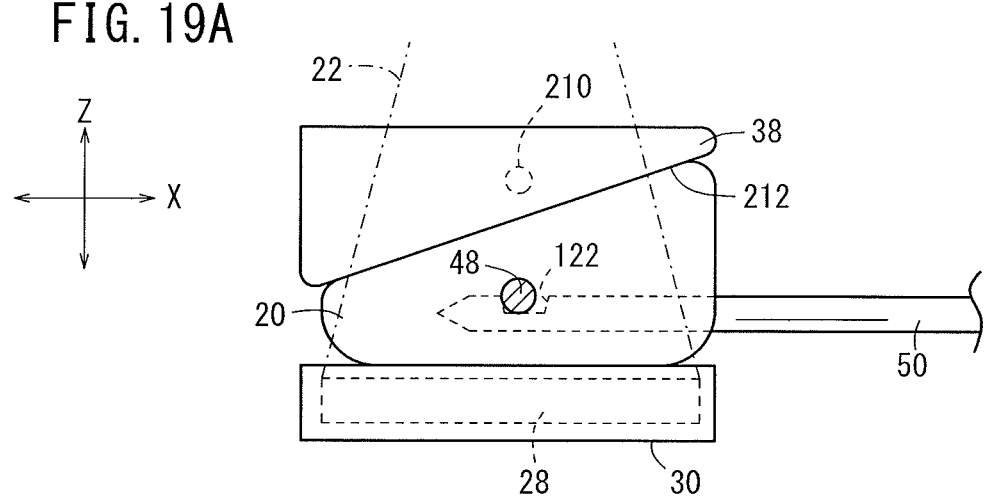
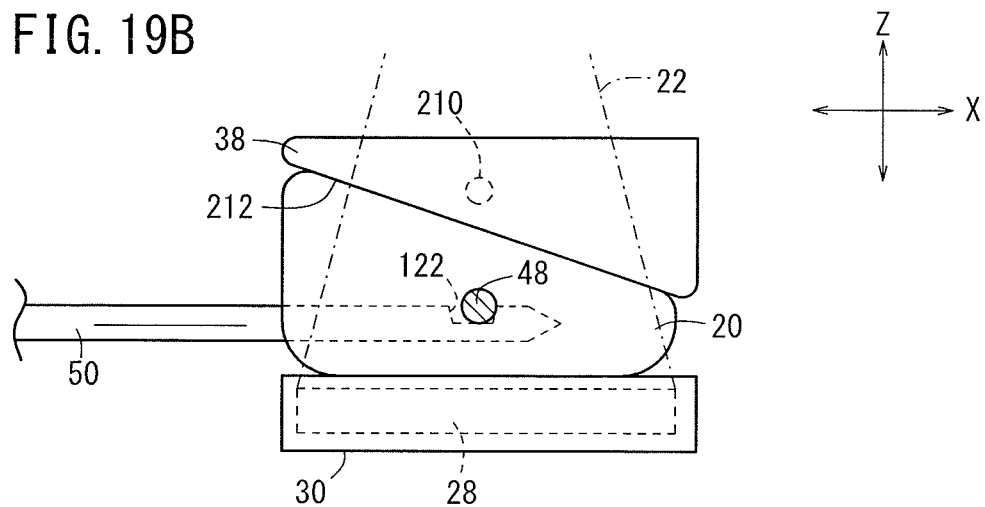

RADIOGRAPHIC IMAGE CAPTURING APPARATUS

CROSS-REFERENCE TO RELATED APPLICATION

This application is based upon and claims the benefit of priority from Japanese Patent Application No. 2011-099367 filed on Apr. 27, 2011, of which the contents are incorporated herein by reference.

BACKGROUND OF THE INVENTION

1. Field of the Invention

The present invention relates to a radiographic image capturing apparatus for compressing a target object to be examined of an examinee, irradiating the target object with radiation, and then detecting and converting radiation that has passed through the target object into a radiographic image.

2. Description of the Related Art

Heretofore, a biopsy procedure has widely been performed in which a sampling needle is inserted into a target object to be examined in order to extract a tissue sample from a test region in the target object. More specifically, a biopsy apparatus for carrying out such a biopsy procedure is incorporated in a radiographic image capturing apparatus for capturing radiographic images of target objects to be examined. The radiographic image capturing apparatus, with the biopsy apparatus incorporated therein, operates in the following manner. A target object to be examined, such as the breast of a patient or a phantom that simulates a breast, is placed on an image capturing base (holding member) and is compressed by a compression plate (compression member), and then the target object is irradiated with radiation. Radiation that has passed through the target object is converted into a radiographic image by a radiation detector. Based on the position of a test region in the target object, which is obtained from the radiographic image, a sampling needle is inserted into the target object to remove a sample tissue of the test region.

Two processes are available in the art for inserting a sampling needle into a target object. According to one of the processes, which may be referred to as a vertical approach process, the sampling needle is inserted through an opening in the compression plate into the target object, along a direction in which the target object is compressed by the compression plate, i.e., along a direction toward the holding member. The other process, which may be referred to as a lateral approach process, inserts the sampling needle laterally into a side area of the target object, which is compressed by the compression plate.

According to the lateral approach process, in a case where the target object is viewed in front elevation, the sampling needle pierces a side area of the target object along a horizontal direction thereof. Therefore, the compression plate does not need to have an opening therein for allowing the sampling needle to pass therethrough. However, since the target object is compressed under uniform pressure along the horizontal direction, in a case where the sampling needle is inserted into the side area of the target object perpendicularly to the direction in which the target object is compressed, the target object is likely to become positionally displaced in a direction away from the side area that is pierced by the sampling needle.

According to the lateral approach process, therefore, compared to the vertical approach process, the pressure applied to compress the target object tends to be stronger, so as to prevent the target object from being unduly positionally displaced. Such increased pressure, which is applied to the target object, poses a greater burden on the target object.

Japanese Laid-Open Patent Publication No. 2009-207681 and U.S. Patent Application Publication No. 2009/0135997 disclose methods of compressing a target object. According to the compressing method disclosed in Japanese Laid-Open Patent Publication No. 2009-207681, a compression plate is tilted along a depth-wise direction of the target object to compress and hold the target object obliquely to the depth-wise direction. The compressing method disclosed in U.S. Patent Application Publication No. 2009/0135997 uses two rods that extend in a depth-wise direction of the target object. The two rods support respective opposite ends of a flexible sheet and are displaced toward the image capturing base until they reach the same height, whereupon the target object held on the image capturing base is covered with the sheet.

SUMMARY OF THE INVENTION

If the compressing method disclosed in Japanese Laid-Open Patent Publication No. 2009-207681 is applied to a radiographic image capturing apparatus in which a lateral approach biopsy procedure is carried out, then since the compression plate, which is tilted along the depth-wise direction of the target object, compresses the target object, the pressure applied to the target object is uniform along the horizontal direction of the target object. If the compressing method disclosed in U.S. Patent Application Publication No. 2009/0135997 is applied to a radiographic image capturing apparatus in which a lateral approach biopsy procedure is carried out, then since two rods are displaced toward the image capturing base until the rods reach the same height, the pressure applied to the target object also is uniform along the horizontal direction of the target object.

Consequently, even if a lateral approach biopsy procedure is applied in order to compress the target object in the disclosed compressing methods, in a case where the sampling needle is inserted into the target object along the horizontal direction, the compressed target object tends to be positionally displaced by the inserted sampling needle.

It is an object of the present invention to provide a radiographic image capturing apparatus, which is capable of preventing a compressed target object from being positionally displaced upon a lateral approach biopsy procedure being performed on the target object.

To achieve the above object, there is provided in accordance with the present invention a radiographic image capturing apparatus comprising a radiation source for applying radiation to a target object to be examined, a radiation detector for detecting radiation that has passed through the target object and for converting the detected radiation into a radiographic image, a holding member for holding the target object, and a compression member, which is capable of being displaced toward the holding member for compressing the target object held by the holding member while the compression member is tilted with respect to the holding member along lateral directions of the target object as viewed in front elevation.

Since the compression member is tilted with respect to the holding member along lateral directions of the target object as viewed in front elevation, the surfaces of the compression member and the holding member, which compress the target object, are tilted with respect to each other across the target object. Therefore, pressure that is applied to the target object from the compression member and the holding member is distributed unevenly along the lateral directions.

If a portion of the target object where the pressure applied to the target object is relatively low is pierced by a sampling needle along one of the lateral directions, then since the other portion of the target object is compressed and held down in position under a relatively high pressure, the target object is prevented from being unduly positionally displaced, despite the piercing force that the target object receives from the sampling needle. As a consequence, the sampling needle is accurately inserted into the target object with respect to a test region therein, whereby the sampling needle can reliably and efficiently remove a sample tissue from the test region.

According to the present invention, therefore, since the compression member compresses the target object held by the holding member while the compression member is tilted with respect to the holding member along the lateral directions of the target object, the pressure that is applied to the target object from the compression member and the holding member is unevenly distributed along the lateral directions. As a result, the compressed target object is prevented from being unduly positionally displaced during a lateral approach biopsy procedure. Further, preventing the compressed target object from being unduly positionally displaced is effective to avoid compressing the target object under excessively high pressure, so that undue stress on the target object can be reduced.

The radiographic image capturing apparatus may further include a sampling needle for piercing a side region of the target object compressed by the compression member along a piercing direction to remove a sample tissue from a test region in the target object, and a tilted direction determiner for determining a tilted direction in which the compression member is tilted with respect to the holding member based on the piercing direction. Therefore, the tilted direction in which the compression member is tilted with respect to the holding member is determined based on the piercing direction along which the side portion of the target object is pierced. Consequently, the target object is effectively prevented from being unduly positionally displaced when the sampling needle pierces the target object.

In a case where the sampling needle pierces the side region of the target object, the tilted direction determiner may determine the tilted direction such that the distance between the holding member and the compression member becomes progressively smaller from the side region of the target object toward an opposite side region thereof. Accordingly, the pressure under which the target object is compressed is relatively low on one side of the target object where the compression member and the holding member are widely spaced from each other, whereas the pressure under which the target object is compressed on the other side of the target object is relatively high where the compression member and the holding member are in close proximity to each other. In a case where the one side of the target object is pierced by the sampling needle along one of the lateral directions, since the other side of the target object is compressed or held down in position under a relatively high pressure, the target object is reliably prevented from being unduly positionally displaced toward the other side along the one lateral direction.

The radiographic image capturing apparatus may further include a piercing direction determiner for determining the piercing direction of the sampling needle with respect to the target object based on a present position of the sampling needle. Since the piercing direction determiner automatically determines the piercing direction, the tilted direction can easily be determined.

The compression member may further comprise a compression plate, which is displaceable from the radiation source toward the holding member, or a compression plate, which is displaceable from the radiation source toward the holding member and a first spacer interposed between the compression plate and the target object, or a compression sheet, which is displaceable from the radiation source toward the holding member. The holding member may comprise an image capturing base that houses the radiation detector therein for holding the target object, or an image capturing base that houses the radiation detector therein for holding the target object and a second spacer, which is interposed between the image capturing base and the target object.

With the compression member and the holding member being constructed as described above, the following arrangements [1] through [9] for the radiographic image capturing apparatus may be provided.

[1] The radiographic image capturing apparatus may include a first rotational shaft extending in a depth-wise direction of the target object and which is coupled to the compression plate, and a rotary actuator for rotating the compression plate about the first rotational shaft, so as to tilt the compression plate with respect to the holding member. The compression plate can thus be easily tilted with respect to the holding member.

[2] The radiographic image capturing apparatus may include a tilted state maintaining mechanism for keeping the compression plate in a tilted state where the compression plate is tilted such that an end or an opposite end thereof is closer to the holding member across the target object as viewed in front elevation. The target object can thus reliably be kept in a compressed state.

[3] In [1] or [2], after the target object has been compressed by the compression plate and the holding member, the compression plate may be tilted with respect to the holding member, or alternatively, after the compression plate has been tilted with respect to the holding member, the target object may be compressed by the tilted compression plate and the holding member. In either case, the target object is compressed and held under an uneven pressure along the lateral directions thereof.

[4] The compression plate may have a surface that faces toward the target object and is constructed as a slanted surface, which is inclined with respect to the holding member, wherein the target object is compressed by the holding member and the slanted surface of the compression plate. In this manner, the target object can be compressed and held under an uneven pressure along the lateral directions thereof, simply by the compression plate being displaced toward the holding member.

[5] The first spacer may have a surface that faces toward the target object and is constructed as a slanted surface, which is inclined with respect to the holding member, wherein the target object is compressed by the holding member and the slanted surface of the first spacer. With this arrangement, the target object can also be compressed and held under an uneven pressure along the lateral directions thereof, simply by the compression plate and the first spacer being displaced toward the holding member.

[6] The second spacer may have a surface that faces toward the target object and is constructed as a slanted surface, which is inclined with respect to the compression member, wherein the target object is compressed by the compression member and the slanted surface of the second spacer. With this arrangement, the target object can also be compressed and held under an uneven pressure along the lateral directions thereof, simply by the compression member being displaced toward the second spacer.

[7] The radiographic image capturing apparatus may further include a first rod, which extends in a depth-wise direction of the target object as viewed in front elevation and supports an end of the compression sheet, a second rod, which extends in the depth-wise direction of the target object and supports an opposite end of the compression sheet, a first rod movement controller for moving the first rod toward and away from the holding member, and a second rod movement controller for moving the second rod toward and away from the holding member.

The compression sheet may be tilted with respect to the holding member in a case where the first rod movement controller moves the first rod with respect to the holding member and the second rod movement controller moves the second rod with respect to the holding member. In this manner, even if the compression sheet is used, the target object can be compressed and held under an uneven pressure along the lateral directions thereof.

[8] In [7], the first rod movement controller and the second rod movement controller may move the first rod and the second rod to respective different heights above the holding member, for thereby tilting the compression sheet with respect to the holding member. In this manner, the target object can be compressed and held under an uneven pressure along the lateral directions thereof.

[9] The radiographic image capturing apparatus may further include a radiation source housing unit housing the radiation source therein, an arm connecting the radiation source housing unit and the image capturing base to each other, a compression member support supporting the compression member for movement with respect to the arm, and a second rotational shaft coupled to the arm.

The arm may be turned about the second rotational shaft to tilt the image capturing base with respect to the compression member. If the arm, the radiation source housing unit, and the image capturing base are turned in unison, the image capturing base is tilted with respect to the compression member for thereby compressing and holding the target object under an uneven pressure along the lateral directions thereof.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 19A and 19B are front elevational views showing the manner in which a biopsy needle is inserted into a breast, which is compressed by a slanted surface of a compression plate and an image capturing base according to a fourth modification;

DESCRIPTION OF THE PREFERRED EMBODIMENTS

Radiographic image capturing apparatus according to preferred embodiments of the present invention will be described in detail below with reference to FIGS. 1 through 28B.
Configuration of the Mammographic Apparatus 10

Figure 1:
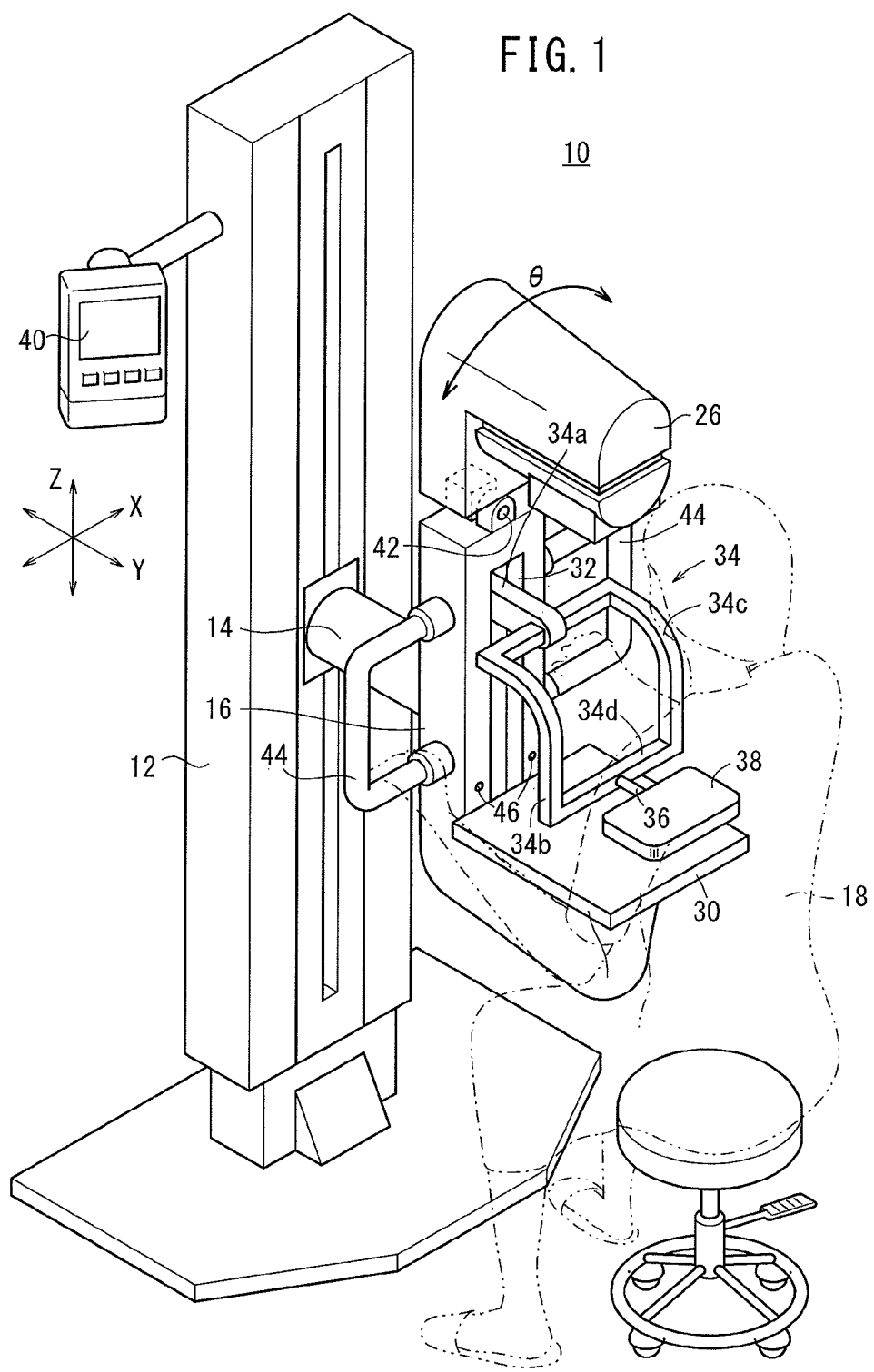
FIG. 1 is a perspective view of a mammographic apparatus as a radiographic image capturing apparatus according to an embodiment of the present invention.
Figure 2:
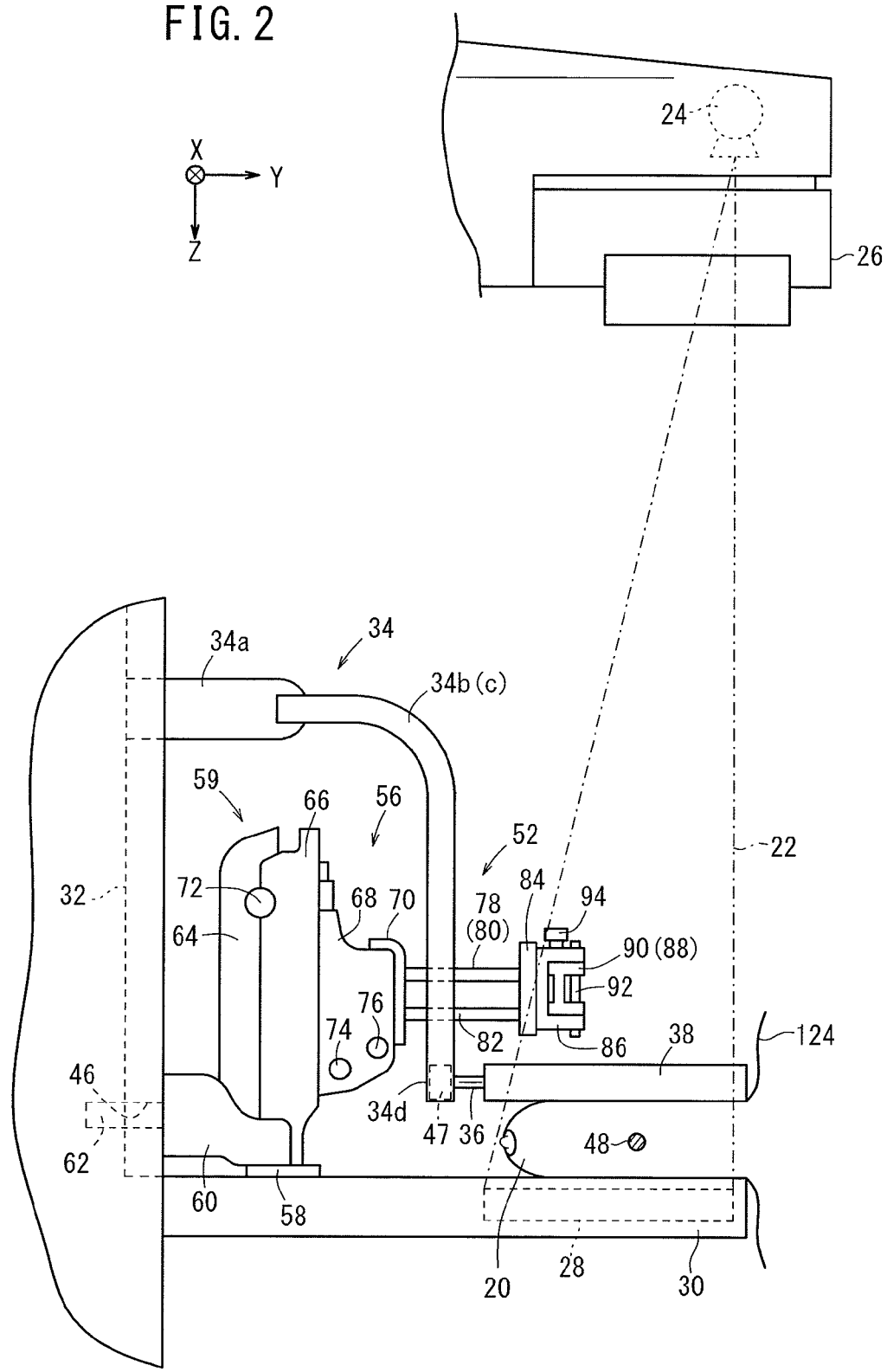
FIG. 2 is an enlarged fragmentary side elevational view of the mammographic apparatus shown in FIG. 1.
Figure 3:
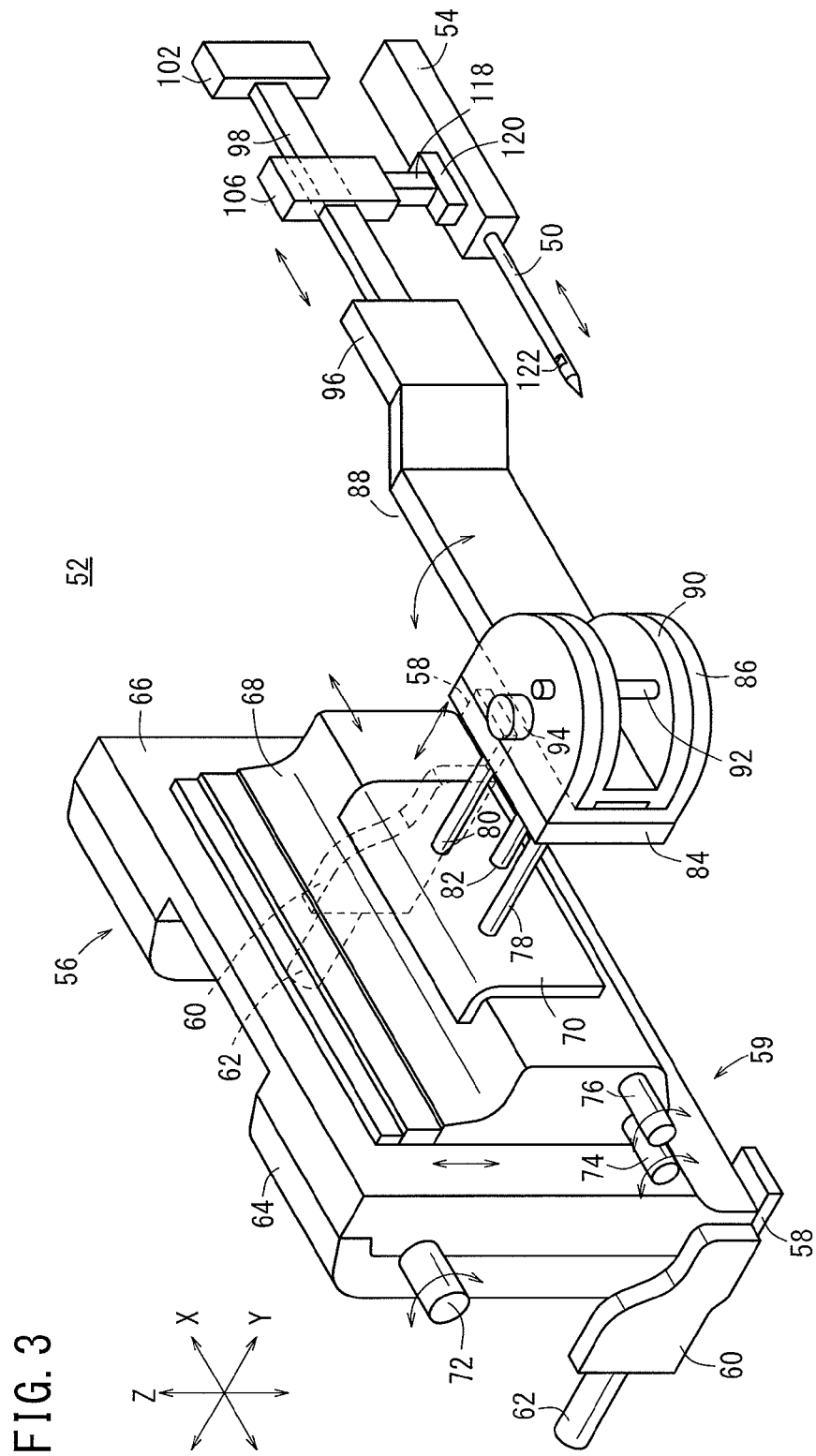
FIG. 3 is a perspective view of a biopsy apparatus including a biopsy needle, which is incorporated in the mammographic apparatus shown in FIG. 1.

As shown in FIGS. 1 and 2, a mammographic apparatus 10, which serves as a radiographic image capturing apparatus according to an embodiment of the present invention, basically includes an upstanding base 12, a vertical arm 16 fixed to the distal end of a horizontal swing shaft 14 (second rotational shaft) disposed substantially centrally on the base 12, a radiation source housing unit 26 accommodating a radiation source 24 therein for applying radiation 22 to a breast 20 (see FIG. 2) as a target object to be examined of an examinee 18, the radiation source housing unit 26 being fixed to an upper end of the arm 16, and an image capturing base 30 (holding member) fixed to a lower end of the arm 16 and housing therein a solid-state detector 28 (see FIG. 2) for detecting radiation 22 that has passed through the breast 20.

The arm 16 has a vertical groove 32 defined in a side surface (front side) thereof, which faces toward the examinee 18 in the direction indicated by the arrow Y and extends in the directions indicated by the arrow Z. A compression plate support 34 is vertically movably supported on the arm 16 for displacement along the groove 32 in the directions indicated by the arrow Z.

The compression plate support 34 includes a proximal end portion 34a inserted in the groove 32 and held in fitting engagement with a mount (not shown) in the groove 32. The proximal end portion 34a is disposed between the radiation source housing unit 26 and the image capturing base 30. The compression plate support 34 also includes two intermediate bars 34b, 34c extending from the free end of the proximal end portion 34a toward the image capturing base 30, and a joint 34d interconnecting distal ends of the intermediate bars 34b, 34c. The joint 34d is coupled to a rotational shaft 36 (first rotational shaft) extending in the direction indicated by the arrow Y (also referred to as a depth-wise direction of the breast 20). A compression plate 38 (compression member) for compressing and holding the breast 20 against the image capturing base 30 is pivotally supported on the distal end of the rotational shaft 36. The joint 34d houses therein a motor 47 (rotary actuator) for rotating the rotational shaft 36 about its axis. By energization of the motor 47, the motor 47 rotates the rotational shaft 36 about its axis, thereby turning the compression plate 38 about the axis of the rotational shaft 36.

To the base 12, there is connected a display control panel 40 for displaying image capturing conditions including an image capturing region, etc., of the examinee 18, ID information of the examinee 18, etc., and for setting such items of information as necessary.

In a case where the arm 16, to which the radiation source housing unit 26 and the image capturing base 30 are secured, is angularly moved about the swing shaft 14, an image capturing direction with respect to the breast 20 of the examinee 18 is adjusted. The radiation source housing unit 26 is coupled to the arm 16 by a hinge 42, so as to be angularly movable in the directions indicated by the arrow θ independently of the image capturing base 30.

Handles 44 are mounted on respective sides of the arm 16, which face away from each other along the directions indicated by the arrow X, i.e., the horizontal direction of the breast 20. The handles 44 are gripped by the examinee 18. The arm 16 has two holes 46 defined in the front side thereof near the image capturing base 30, one on each side of the groove 32.

As shown in FIGS. 2 through 5, the mammographic apparatus 10 incorporates therein a biopsy apparatus 52 having a biopsy needle 50 (sampling needle) for sampling a sample tissue from a biopsy region 48 (test region) of the breast 20. The biopsy apparatus 52 includes a biopsy needle mount 54 with the biopsy needle 50 mounted thereon, and a biopsy needle moving mechanism 56 for moving the biopsy needle mount 54 in order to position the biopsy needle 50 at a desired position. In FIG. 1, the biopsy apparatus 52 is omitted from illustration.

The biopsy needle moving mechanism 56 includes a main unit 59 disposed on the image capturing base 30 with two base members 58 interposed therebetween.

Two arms 60 are mounted on respective side surfaces of the main unit 59, which face away from each other along the directions indicated by the arrow X. The arms 60 extend toward the arm 16 and have respective rods 62 that fit into respective holes 46 provided in the arm 16. The main unit 59, which is disposed on the image capturing base 30 with the two base members 58 interposed therebetween and with the two rods 62 fitted into the respective holes 46, is fixed in position between the arm 16 and the intermediate bars 34b, 34c, such that the main unit 59 is disposed in facing relation to the examinee 18.

The main unit 59 includes an upstanding rear member 64, which extends in the directions indicated by the arrow Z and is disposed near the arm 16, a front member 66 mounted on a front side of the rear member 64 (facing the examinee 18), a moving unit 68 mounted on a front side of the front member 66, and another moving unit 70 mounted on a front side of the moving unit 68. A knob 72 is disposed on a side surface of the main unit 59, at the boundary between the rear member 64 and the front member 66. Two knobs 74, 76 are disposed on a side surface of the moving unit 68. Three rods 78, 80, 82 are mounted on a front side of the moving unit 70 and extend along the directions indicated by the arrow Y. A flat holder 84 is mounted on distal ends of the rods 78, 80, 82.

The rear member 64 comprises a thin member having a relatively large recess defined therein that faces toward the examinee 18. The front member 66 also is a thin member having a relatively large recess defined therein that faces toward the arm 16. In a case where the front member 66 is mounted on the rear member 64, the respective recesses jointly make up a relatively large closed space in the main unit 59, which accommodates a moving mechanism therein comprising machine elements (not shown) for moving the biopsy needle 50.

The moving unit 68 is capable of being moved by the moving mechanism in directions indicated by the arrow Z with respect to the front member 66. The moving unit 70 is capable of being moved by the moving mechanism in directions indicated by the arrow X with respect to the moving unit 68. The holder 84 is movable in directions indicated by the arrow Y upon the rods 78, 80, 82 being moved by the moving mechanism in directions indicated by the arrow Y. Machine elements of the moving mechanism may be made up from gears, worm gears, racks, and pinions of a known nature for moving the various components of the main unit 59 referred to above in respective directions indicated by the arrows X, Y, Z.

The knobs 72, 74, 76 are operatively coupled to the moving mechanism. In a case where a doctor or radiological technician who handles the mammographic apparatus 10 turns the knob 72, rotational power from the knob 72 is transmitted to the moving mechanism, which then displaces the moving unit 68 in the directions indicated by the arrow Z. In a case where the doctor or radiological technician turns the knob 74, rotational power of the knob 74 is transmitted to the moving mechanism, which then displaces the moving unit 70 in the directions indicated by the arrow X. In a case where the doctor or radiological technician turns the knob 76, rotational power from the knob 76 is transmitted to the moving mechanism, which then displaces the rods 78, 80, 82 in the directions indicated by the arrow Y.

An arm support 86, which is U-shaped as viewed in side elevation in FIG. 2, is fixed to the holder 84. An arm 88, which extends in the directions indicated by the arrow X, has an end 90 pivotally supported on the arm support 86.

More specifically, the arm support 86 comprises a U-shaped component including a flat member attached to the holder 84, and a pair of upper and lower wings that project from respective upper and lower ends of the flat member toward the examinee 18. The end 90 of the arm 88 is substantially U-shaped and is held in contact with inner surfaces of the arm support 86. A vertical pivot pin 92 extends through the upper and lower wings of the arm support 86 and through the U-shaped end 90 of the arm 88, thereby joining the arm support 86 and the arm 88 to each other. The U-shaped end 90 of the arm 88 is angularly movable about the pivot pin 92.

A knob 94 is disposed on the upper wing of the arm support 86 and extends therethrough so as to come into abutment against the end 90 of the arm 88. The knob 94 is externally threaded and held in threaded engagement with an internally threaded surface of the upper wing of the arm support 86. In a case where the doctor or radiological technician turns the knob 94 until the lower end of the knob 94 abuts against the end 90 of the arm 88, both the arm 88 and the end 90 of the arm 88 are secured in position angularly about the pivot pin 92.

The arm 88 has another end 96, to which a rectangular rod 98 is fixed that extends in the directions indicated by the arrow X. The rod 98 has a distal end joined to an end block 102. A slider 106 is slidably supported on the rod 98 for sliding movement between the other end 96 and the end block 102. The slider 106 may be moved automatically by a motor-driven cylinder, or may be displaced manually by the doctor or radiological technician.

The slider 106 is coupled to an attachment 120 in the form of a flat plate by a support member 118, which extends downwardly from the slider 106 toward the image capturing base 30. The biopsy needle mount 54 is attached to the attachment 120.

The biopsy needle 50 includes a sampler 122 for attracting and sampling tissue, such as calcified tissue, from the biopsy region 48 of the breast 20.

As described above, upon actuation of the moving mechanism in the main unit 59, the biopsy needle moving mechanism 56 moves the moving unit 68 in the directions indicated by the arrow Z, moves the moving unit 70 in the directions indicated by the arrow X, and moves the rods 78, 80, 82 together with the holder 84 in the directions indicated by the arrow Y. The end 90 of the arm 88 is pivotally supported by the pivot pin 92, which extends through the arm support 86 that is fixed to the holder 84. The slider 106 is slidable in the directions indicated by the arrow X along the rod 98, which extends between and is joined to the other end 96 of the arm 88 and the end block 102. The biopsy needle mount 54, with the biopsy needle 50 mounted thereon, is connected to the slider 106 by the support member 118 and the attachment 120.

Accordingly, if the moving mechanism in the main unit 59 is actuated, the biopsy needle 50 is moved in respective directions indicated by the arrows X, Y, Z, and if the slider 106 is slidably displaced along the rod 98 between the other end 96 of the arm 88 and the end block 102, the biopsy needle 50 is moved in the directions indicated by the arrow X. If the end 90 of the arm 88 is angularly moved about the pivot pin 92, the biopsy needle 50 is moved angularly in the X-Y plane, i.e., a plane defined by the arrows X and Y.

Figure 4:
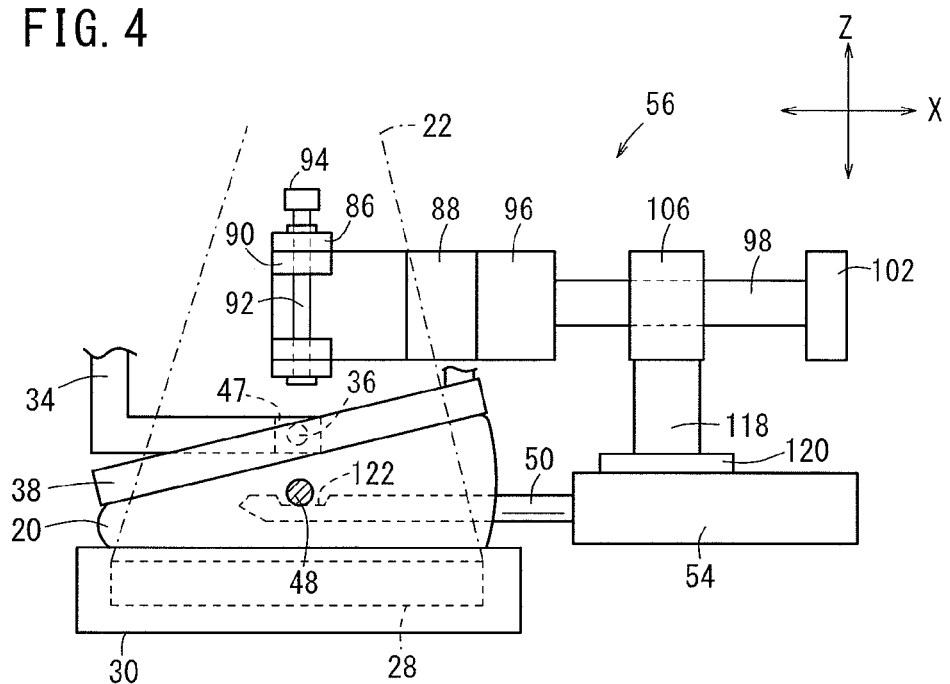
FIG. 4 is a front elevational view showing the manner in which a biopsy needle is inserted into a compressed breast.

According to the present embodiment, as shown in FIG. 4, in a case where the breast 20 is viewed in front elevation from the chest wall 124 (see FIG. 2) of the examinee 18, the compression plate 38 is tilted with respect to the image capturing base 30 along the directions indicated by the arrow X, i.e., along lateral or horizontal directions of the breast 20. If the breast 20 is compressed by the compression plate 38, which is tilted as described above, pressure applied to the breast 20 from the compression plate 38 and the image capturing base 30 is unevenly distributed along the directions indicated by the arrow X.

More specifically, as shown in FIG. 4, upon the motor 47 being energized to turn the rotational shaft 36 about its axis and to tilt the compression plate 38 downward to the left with respect to the image capturing base 30, i.e., counterclockwise about the rotational shaft 36, the left area of the compression plate 38 is brought into close proximity to the image capturing base 30, whereas the right area of the compression plate 38 remains spaced away from the image capturing base 30. Therefore, pressure applied to the breast 20 from the compression plate 38 and the image capturing base 30 is relatively high at the left region of the breast 20, and is relatively low at the right region of the breast 20.

Figure 5:
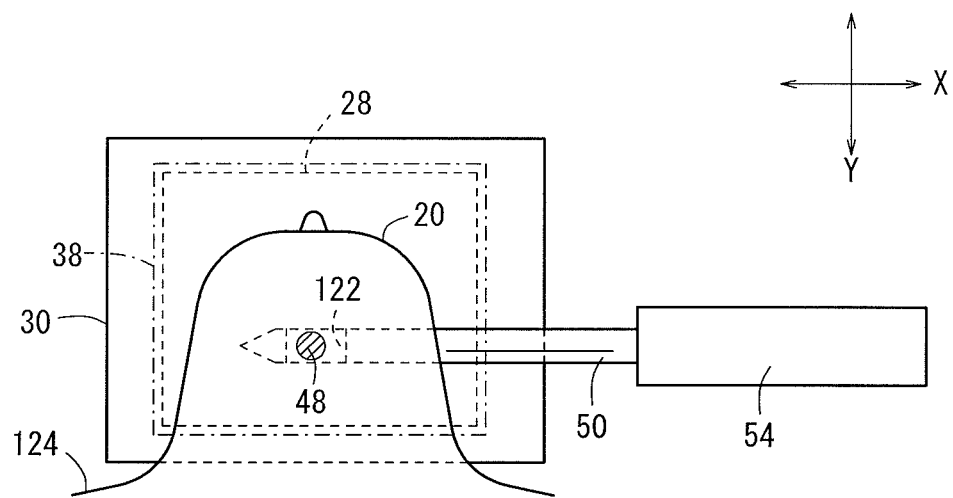
FIG. 5 is a plan view showing the manner in which the biopsy needle is inserted into the compressed breast.

As shown in FIGS. 4 and 5, if a lateral approach biopsy procedure is carried out to insert the biopsy needle 50 laterally into the right region of the breast 20 where the applied pressure is relatively low, since the left region of the breast 20 where the applied pressure is relatively high is compressed firmly by the compression plate 38 and the image capturing base 30, the breast 20 is prevented from being unduly positionally displaced by the force (piercing force) applied from the biopsy needle 50 to the breast 20 in the leftward direction, as indicated by the arrow X.

Different examples by which the breast 20 is compressed in the mammographic apparatus 10 shown in FIGS. 1 through 5 will be described below with reference to FIGS. 6A through 9C. In FIGS. 6A through 9C, certain components are schematically illustrated for the purpose of explaining characteristic functions of the present embodiment, i.e., functions for compressing the breast 20 with the compression plate 38, which is tilted with respect to the image capturing base 30.

FIGS. 6A through 7C show two examples in which the image capturing base 30 and the compression plate 38, which lie parallel to each other along the directions indicated by the arrow X, compress the breast 20 therebetween, and thereafter, the compression plate 38 is tilted relatively to the image capturing base 30 to compress the breast 20 while the compression plate 38 remains in a tilted condition.

Figure 6A:
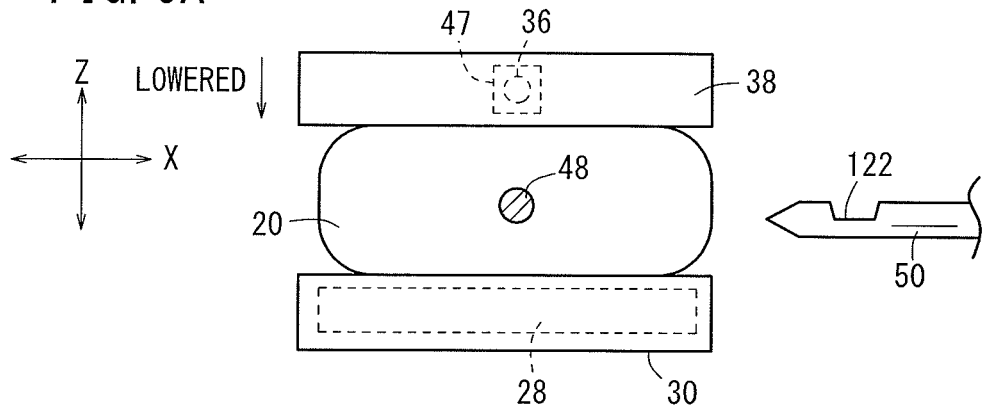
FIG. 6A is a front elevational view showing the manner in which the breast is compressed by a compression plate and an image capturing base.
Figure 6B:
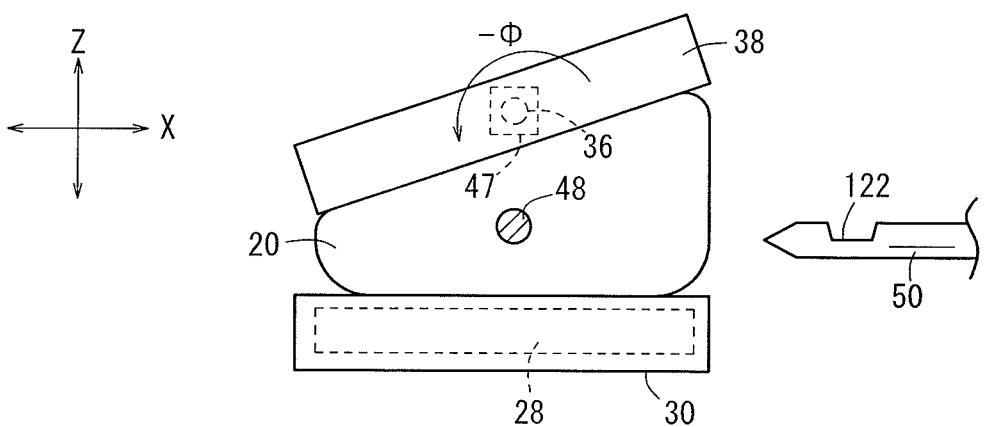
FIG. 6B is a front elevational view showing the manner in which the breast is compressed by the compression plate, which is tilted with respect to the image capturing base.
Figure 6C:
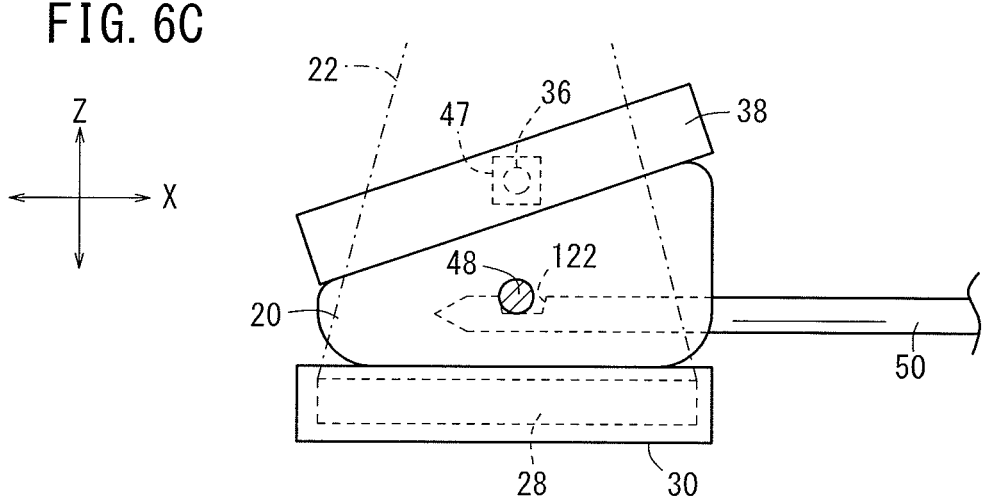
FIG. 6C is a front elevational view showing the manner in which the biopsy needle is inserted into the compressed breast.

In the example shown in FIGS. 6A through 6C, the compression plate 38 is tilted downward to the left with respect to the image capturing base 30 along the directions indicated by the arrow X, so as to compress the breast 20 while the compression plate 38 is in a tilted state.

More specifically, the image capturing base 30 and the compression plate 38 initially lie parallel to each other along the directions indicated by the arrow X with the breast 20 interposed therebetween. Then, as shown in FIG. 6A, the compression plate 38 is lowered toward the image capturing base 30, thereby compressing and holding the breast 20 on the image capturing base 30. At this time, since the image capturing base 30 and the compression plate 38 lie parallel to each other, pressure that is applied to the breast 20 from the compression plate 38 and the image capturing base 30 is uniformly distributed along the directions indicated by the arrow X.

While the breast 20 is being compressed as described above, the motor 47 is energized to turn the rotational shaft 36 about its axis counterclockwise in a −Φ direction, as shown in FIG. 6B. The compression plate 38 also is turned in the −Φ direction and is tilted downward to the left in FIG. 6B with respect to the image capturing base 30. As a result, the breast 20 is compressed obliquely downward to the left by the tilted compression plate 38 and the image capturing base 30. Consequently, pressure that is applied to the breast 20 from the compression plate 38 and the image capturing base 30 is relatively high at the left region of the breast 20, and is relatively low at the right region of the breast 20 along the directions indicated by the arrow X, and hence the pressure is unevenly distributed along the directions indicated by the arrow X.

While the breast 20 is compressed obliquely downward to the left, as shown in FIG. 6C, the biopsy needle 50 is inserted into the right region of the breast 20 along the leftward direction as indicated by the arrow X. Since the left region of the breast 20 is compressed firmly under a higher pressure by the compression plate 38 and the image capturing base 30, which are in close proximity to each other, even if a piercing force is applied to the breast 20 from the biopsy needle 50 while piercing the right region of the breast 20 along the leftward direction as indicated by the arrow X, the breast 20 is prevented from being unduly positionally displaced to the left in FIG. 6C.

As shown in FIG. 6C, radiation 22 is applied to the breast 20 in order to acquire a radiographic image of the breast. However, radiation 22 may be applied to the breast 20 in order to acquire a radiographic image while the breast 20 is compressed by the compression plate 38 and the image capturing base 30, which lie parallel to each other, as shown in FIG. 6A. Radiation is not applied to the breast 20 while the compression plate 38 undergoes movement or is turned, or while the biopsy needle 50 undergoes movement.

Figure 7A:
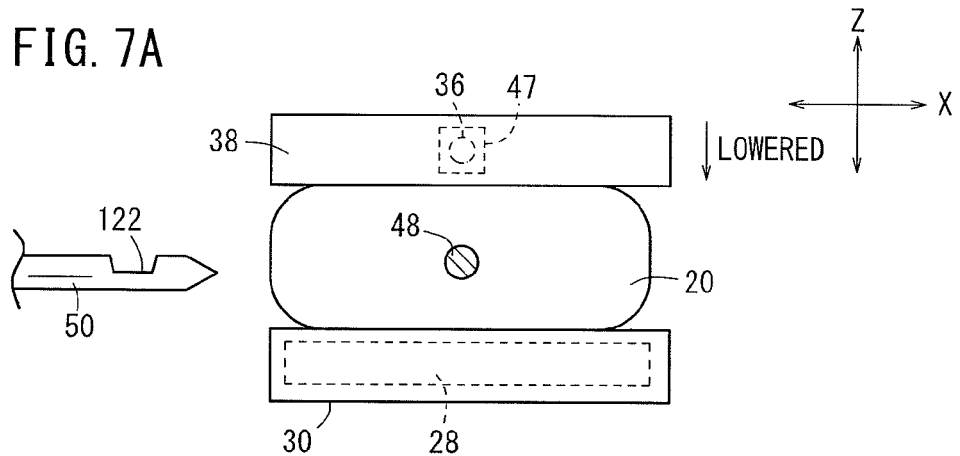
FIG. 7A is a front elevational view showing the manner in which the breast is compressed by the compression plate and the image capturing base.
Figure 7B:
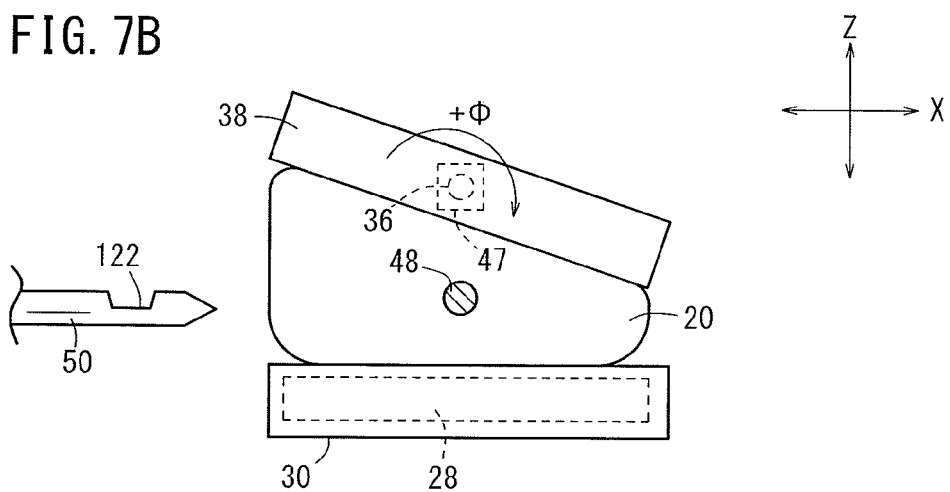
FIG. 7B is a front elevational view showing the manner in which the breast is compressed by the compression plate, which is tilted with respect to the image capturing base.
Figure 7C:
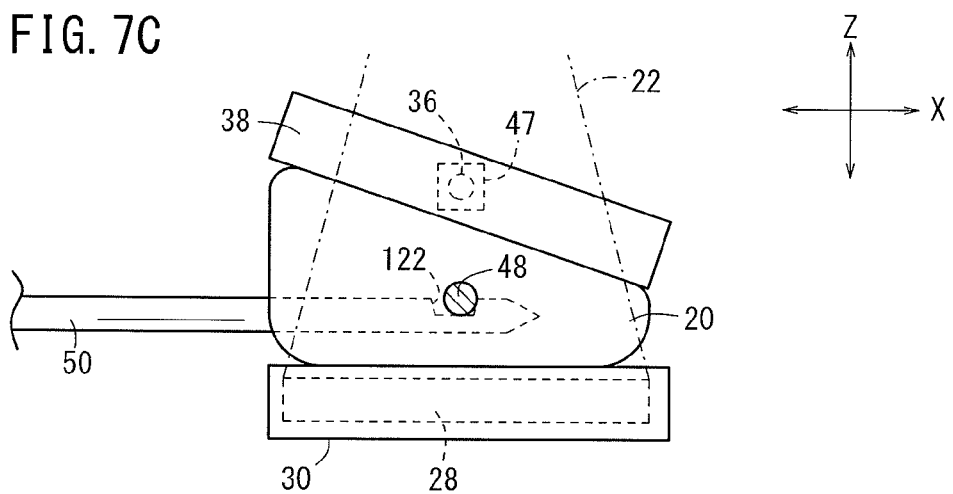
FIG. 7C is a front elevational view showing the manner in which the biopsy needle is inserted into the compressed breast.

In the example shown in FIGS. 7A through 7C, the compression plate 38 is tilted downward to the right with respect to the image capturing base 30 along the directions indicated by the arrow X, whereupon the compression plate 38 compresses the breast 20 while the compression plate 38 is in a tilted state. Basically, in FIGS. 7A through 7C, the compression plate 38 and the biopsy needle 50 move in patterns, which are a reversal of the movement of the compression plate 38 and the biopsy needle 50 shown in FIGS. 6A through 6C.

More specifically, the image capturing base 30 and the compression plate 38 initially lie parallel to each other along the directions indicated by the arrow X with the breast 20 interposed therebetween. Then, as shown in FIG. 7A, the compression plate 38 is lowered toward the image capturing base 30, thereby compressing and holding the breast 20 on the image capturing base 30. Then, the motor 47 is energized to turn the rotational shaft 36 about its axis clockwise in a +Φ direction, as shown in FIG. 7B. Thus, the compression plate 38 is tilted downward to the right in FIG. 7B with respect to the image capturing base 30. As a result, the breast 20 is compressed obliquely downward to the right by the tilted compression plate 38 and the image capturing base 30. Consequently, pressure that is applied to the breast 20 from the compression plate 38 and the image capturing base 30 is relatively high at the right region of the breast 20, and is relatively low at the left region of the breast 20, along the directions indicated by the arrow X. Hence, the pressure is distributed unevenly along the directions indicated by the arrow X. Then, as shown in FIG. 7C, the biopsy needle 50 is inserted into the left region of the breast 20 along the rightward direction indicated by the arrow X. Since the right region of the breast 20 is compressed firmly under higher pressure by the compression plate 38 and the image capturing base 30, which are in close proximity to each other, even if a piercing force is applied to the breast 20 from the biopsy needle 50, which pierces the right region of the breast 20 along the leftward direction indicated by the arrow X, the breast 20 is prevented from being unduly positionally displaced to the right in FIG. 7C.

FIGS. 8A through 9C show two examples, which differ from the two examples shown in FIGS. 6A through 7C, in that the compression plate 38, which is spaced from the breast 20 and the image capturing base 30, is tilted with respect to the image capturing base 2 along the directions indicated by the arrow X, whereupon the breast 20 is compressed obliquely by the tilted compression plate 38 and the image capturing base 30.

Figure 8A:
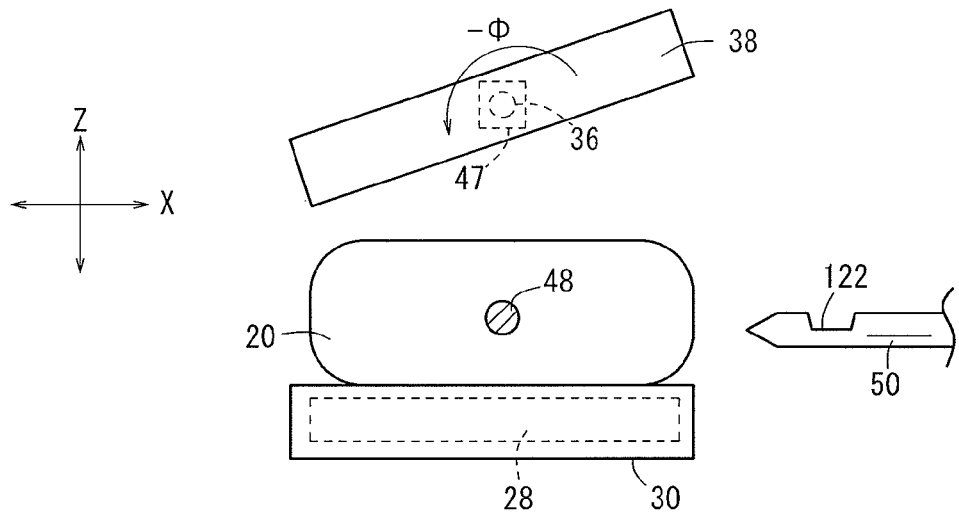
FIG. 8A is a front elevational view showing the manner in which the compression plate is tilted with respect to the image capturing base.
Figure 8B:
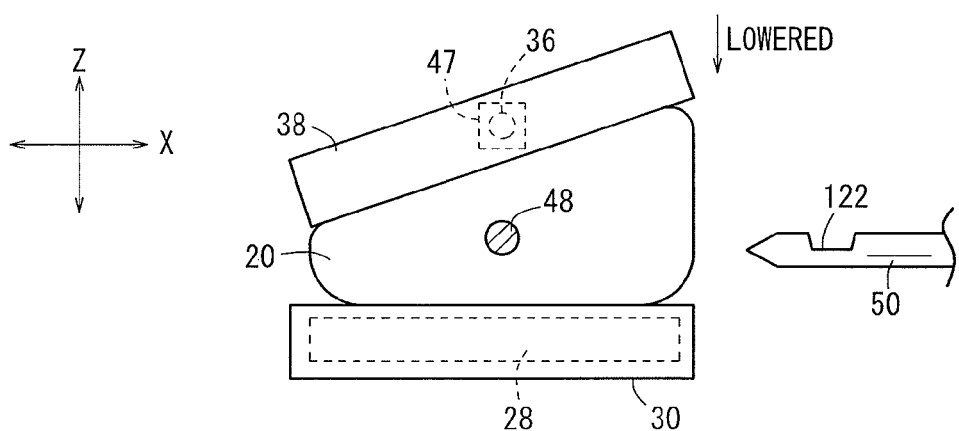
FIG. 8B is a front elevational view showing the manner in which the breast is compressed by the tilted compression plate and the image capturing base.
Figure 8C:
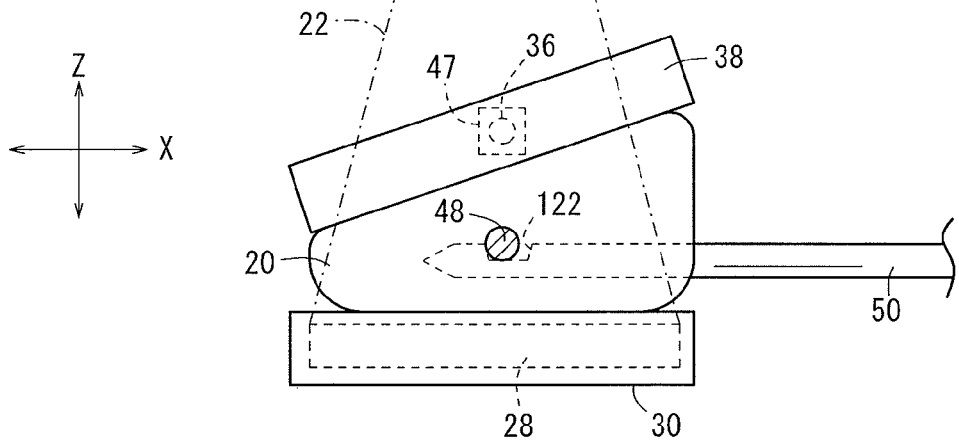
FIG. 8C is a front elevational view showing the manner in which the biopsy needle is inserted into the compressed breast.

In the example shown in FIGS. 8A through 8C, the compression plate 38 is tilted downward to the left with respect to the image capturing base 30 along the directions indicated by the arrow X. The compression plate 38 compresses the breast 20 while the compression plate 38 is in a tilted state.

As shown in FIG. 8A, while the compression plate 38 is spaced from the image capturing base 30, the motor 47 is energized to turn the rotational shaft 36 about its axis counterclockwise in the −Φ direction. The compression plate 38 is also turned in the −Φ direction, and tilted downward to the left in FIG. 8B with respect to the image capturing base 30. Then, the tilted compression plate 38 is lowered toward the image capturing base 30, thereby compressing and holding the breast 20 on the image capturing base 30. At this time, the breast 20 is compressed obliquely downward to the left in FIG. 8B by the tilted compression plate 38 and the image capturing base 30. Consequently, pressure applied to the breast 20 from the compression plate 38 and the image capturing base 30 is relatively high at the left region of the breast 20 and relatively low at the right region of the breast 20 along the directions indicated by the arrow X, and hence the pressure is distributed unevenly along the directions indicated by the arrow X. Then, as shown in FIG. 8C, the biopsy needle 50 is inserted into the right region of the breast 20 along the leftward direction indicated by the arrow X. Since the left region of the breast 20 is compressed firmly under the higher pressure by the compression plate 38 and the image capturing base 30, which are brought into close proximity with each other, even if a piercing force is applied to the breast 20 from the biopsy needle 50, which pierces the right region of the breast 20 along the leftward direction indicated by the arrow X, the breast 20 is prevented from being unduly positionally displaced to the left in FIG. 8C.

Figure 9A:
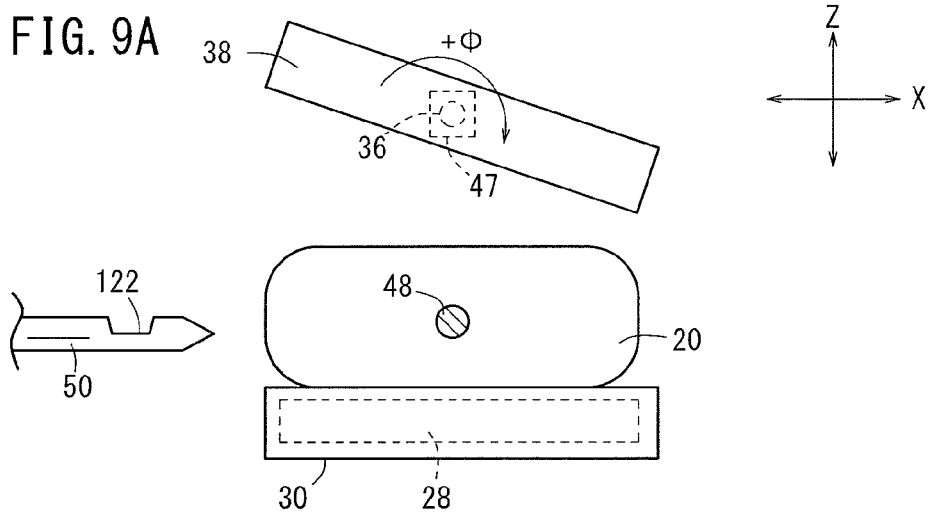
FIG. 9A is a front elevational view showing the manner in which the compression plate is tilted with respect to the image capturing base.
Figure 9B:
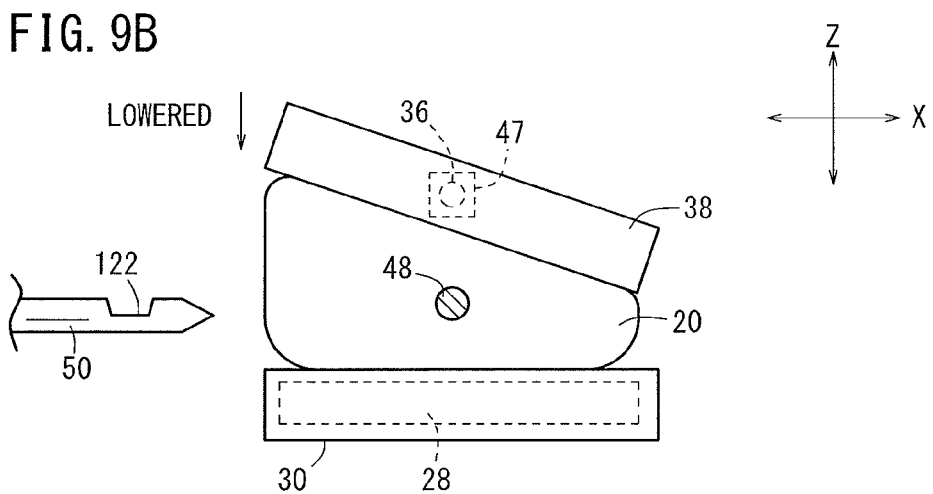
FIG. 9B is a front elevational view showing the manner in which the breast is compressed by the tilted compression plate and the image capturing base.
Figure 9C:
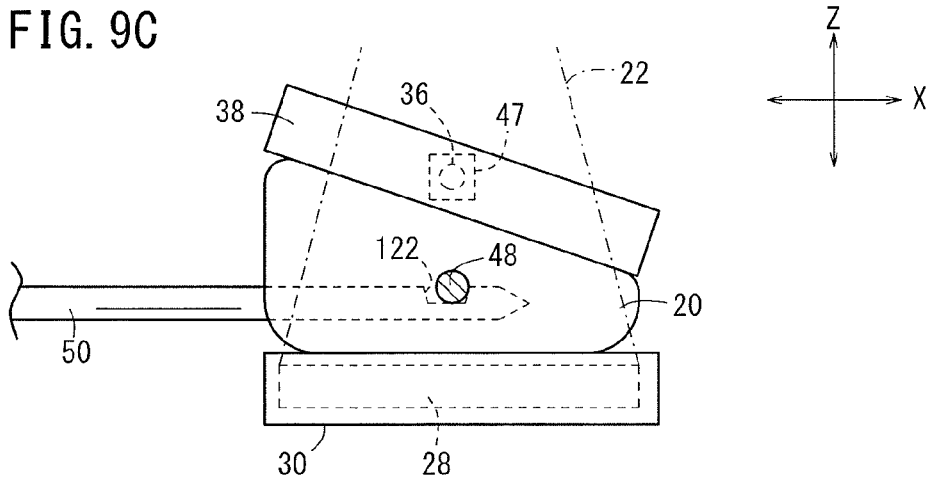
FIG. 9C is a front elevational view showing the manner in which the biopsy needle is inserted into the compressed breast.

In the example shown in FIGS. 9A through 9C, the compression plate 38 is tilted downward to the right with respect to the image capturing base 30 along the directions indicated by the arrow X, and the compression plate 38 compresses the breast 20 while the compression plate 38 is tilted. Basically, in FIGS. 9A through 9C, the compression plate 38 and the biopsy needle 50 move in patterns, which are a reversal of the movement of the compression plate 38 and the biopsy needle 50 shown in FIGS. 8A through 8C.

As shown in FIG. 9A, while the compression plate 38 is spaced from the image capturing base 30, the motor 47 is energized to turn the rotational shaft 36 about its axis counterclockwise in the +Φ direction, thereby tilting the compression plate 38 downward to the right in FIG. 9A with respect to the image capturing base 30. Then, as shown in FIG. 9B, the tilted compression plate 38 is lowered toward the image capturing base 30, thereby compressing and holding the breast 20 on the image capturing base 30. The breast 20 is compressed obliquely downward to the right in FIG. 9B by the tilted compression plate 38 and the image capturing base 30. Consequently, pressure that is applied to the breast 20 from the compression plate 38 and the image capturing base 30 is relatively high at the right region of the breast 20 and relatively low at the left region of the breast 20 along the directions indicated by the arrow X, and hence the pressure is distributed unevenly along the directions indicated by the arrow X. Then, as shown in FIG. 9C, the biopsy needle 50 is inserted into the left region of the breast 20 along the rightward direction indicated by the arrow X. Since the right region of the breast 20 is strongly compressed under the higher pressure by the compression plate 38 and the image capturing base 30, which are brought into close proximity with each other, even if the piercing force is applied to the breast 20 from the biopsy needle 50, which pierces the left region of the breast 20 along the leftward direction indicated by the arrow X, the breast 20 is prevented from being unduly positionally displaced to the right in FIG. 9C.

Figure 10:
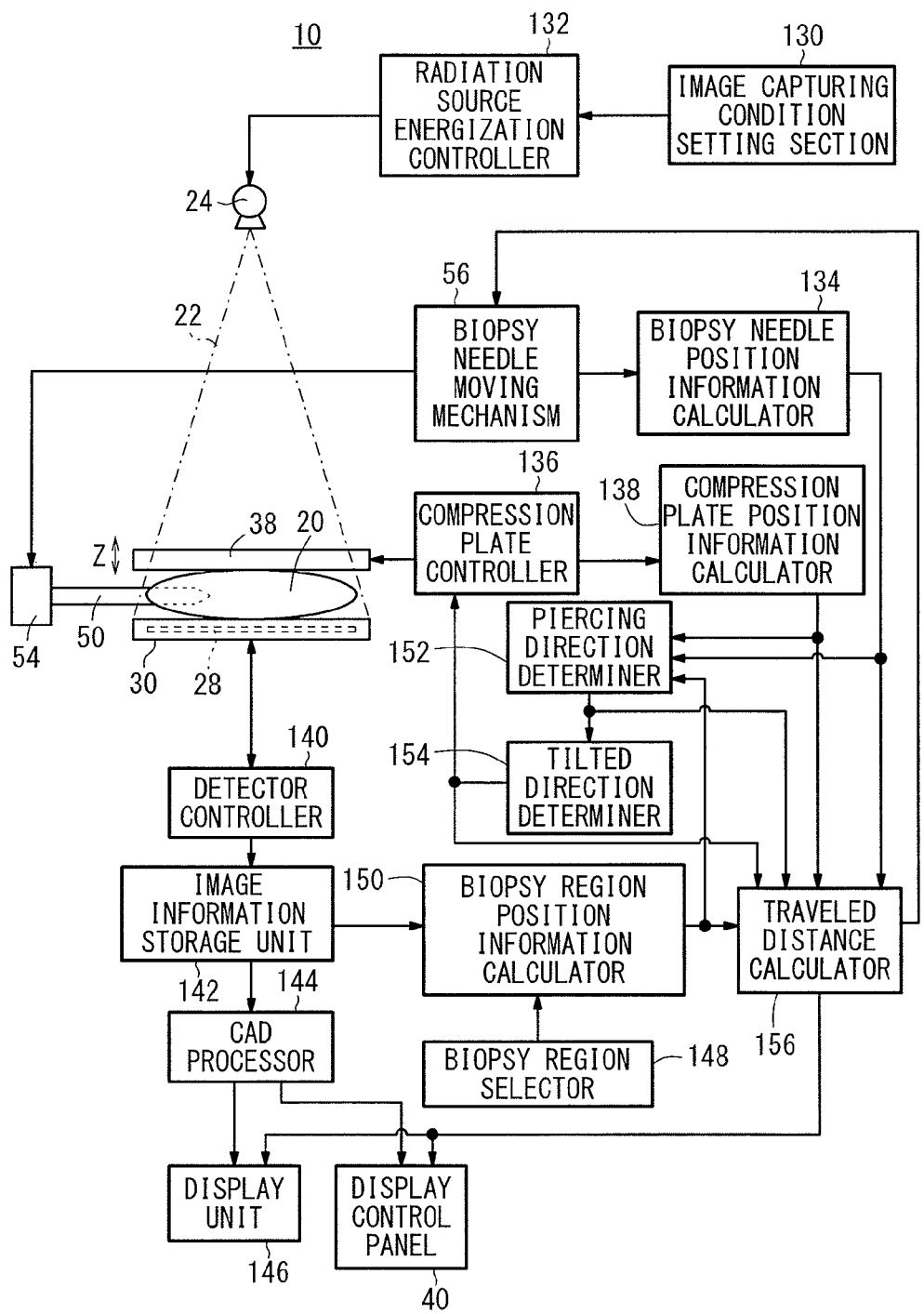
FIG. 10 is a block diagram of the mammographic apparatus shown in FIG. 1.

FIG. 10 shows in block form the mammographic apparatus 10 shown in FIG. 1.

As shown in FIG. 10, the mammographic apparatus 10 includes an image capturing condition setting section 130, a radiation source energization controller 132, a biopsy needle position information calculator 134, a compression plate controller 136, a compression plate position information calculator 138, a detector controller 140, an image information storage unit 142, a CAD (computer aided diagnosis) processor 144, a display unit 146, a biopsy region selector 148, a biopsy region position information calculator 150, a piercing direction determiner 152, a tilted direction determiner 154, and a traveled distance calculator 156.

The image capturing condition setting section 130 sets image capturing conditions including a tube current and a tube voltage of the radiation source 24, an irradiation dose and an irradiation time for the radiation 22, an image capturing method, and an image capturing sequence, etc. The radiation source energization controller 132 controls energization of the radiation source 24 according to the image capturing conditions.

Once the biopsy needle moving mechanism 56 has moved and/or turned the biopsy needle 50 to a certain position, the biopsy needle moving mechanism 56 outputs information concerning the distance that the biopsy needle 50 has moved or turned, e.g., information concerning the angular displacement of gears or the like of the non-illustrated moving mechanism, to the biopsy needle position information calculator 134. Based on such information from the biopsy needle moving mechanism 56, the biopsy needle position information calculator 134 calculates the three-dimensional position (present position) of the tip end of the biopsy needle 50.

The compression plate controller 136 moves the compression plate support 34 and the compression plate 38 in directions indicated by the arrow Z and/or energizes the motor 47 in order to turn the compression plate 38 about the rotational shaft 36 in the +Φ direction or the −Φ direction. The compression plate position information calculator 138 calculates the position of the compression plate 38, which has been moved and/or turned by the compression plate controller 136 with respect to the image capturing base 30. Since the compression plate 38 compresses and holds the breast 20 with respect to the image capturing base 30, the position information of the compression plate 38 represents the thickness of the breast 20 as the breast 20 is compressed, and the tilt angle at which the compression plate 38 is tilted with respect to the image capturing base 30.

The detector controller 140 controls the solid-state detector 28 to acquire a radiographic image of the breast 20, which is converted from the radiation 22, and stores the acquired radiographic image in the image information storage unit 142. The CAD processor 144 processes the radiographic image stored in the image information storage unit 142, and displays the processed radiographic image on the display unit 146 and the display control panel 40.

The mammographic apparatus 10 performs either a scout image capturing process, in which the radiation source 24, which is disposed on the vertical axis (i.e., along the directions indicated by the arrow Z) of the solid-state detector 28, applies radiation 22 to the breast 20, or a stereographic image capturing process, in which the radiation source 24, which is disposed at certain angles after the radiation source housing unit 26 has been turned along the directions indicated by the arrow θ, applies radiation 22 to the breast 20. The solid-state detector 28 detects radiation 22 that has passed through the breast 20 in the scout image capturing process or the stereographic image capturing process, and converts the detected radiation 22 into one or more radiographic images.

In the scout image capturing process, one radiographic image, which is captured when the radiation source 24 is disposed at one image capturing angle ($\theta=0°$) is stored in the image information storage unit 142. In the stereographic image capturing process, two radiographic images, which are captured when the radiation source 24 is disposed at two respective image capturing angles (two angles, i.e., stereographic angles, taken from among the angles $\theta=0°$, $+\theta$, and $-\theta$) are stored in the image information storage unit 142.

The biopsy region selector 148 comprises a pointing device such as a mouse or the like. The doctor or radiological technician in charge who has viewed the displayed contents (e.g., two radiographic images produced by the stereographic image capturing process) on the display unit 146 and/or the display control panel 40 can select one of a plurality of biopsy regions 48 in the displayed two radiographic images from which tissue is to be removed, using the pointing device as the biopsy region selector 148. More specifically, the doctor or radiological technician selects a biopsy region 48 in one of the two radiographic images, and also selects a corresponding biopsy region 48 in the other of the two radiographic images.

The biopsy region position information calculator 150 calculates the three-dimensional position of the biopsy region 48 based on positions of the biopsy region 48 that have been selected in the two radiographic images by the biopsy region selector 148. The three-dimensional position of the biopsy region 48 can be calculated according to a known three-dimensional position calculating scheme for stereographic image capturing processes.

The piercing direction determiner 152 judges the piercing direction in which the biopsy needle 50 pierces the breast 20 based on the three-dimensional position of the tip end of the biopsy needle 50, which has been calculated by the biopsy needle position information calculator 134, the position of the compression plate 38, which has been calculated by the compression plate position information calculator 138, and/or the three-dimensional position of the biopsy region 48, which has been calculated by the biopsy region position information calculator 150.

More specifically, since the direction in which the biopsy needle 50 pierces the breast 20 can be estimated from the positional relationship between the tip end of the biopsy needle 50 and the compression plate 38, the piercing direction determiner 152 specifies the piercing direction in which the biopsy needle 50 pierces the breast 20, using the three-dimensional position of the tip end of the biopsy needle 50 and the position of the breast 20, based on the position of the compression plate 38.

Furthermore, since the piercing direction in which the biopsy needle 50 pierces the breast 20 can be estimated from the positional relationship between the tip end of the biopsy needle 50 and the compression plate 38, the piercing direction determiner 152 can also specify the piercing direction in which the biopsy needle 50 pierces the breast 20 based on the three-dimensional position of the tip end of the biopsy needle 50 and the three-dimensional position of the biopsy region 48, which has been calculated by the biopsy region position information calculator 150.

Moreover, the piercing direction determiner 152 can also specify the piercing direction in which the biopsy needle 50 pierces the breast 20 based on the three-dimensional position of the tip end of the biopsy needle 50, the position of the compression plate 38, and the three-dimensional position of the biopsy region 48.

The tilted direction determiner 154 determines the tilted direction in which the compression plate 38 is tilted with respect to the image capturing base 30, based on the piercing direction in which the biopsy needle 50 pierces the breast 20, as determined by the piercing direction determiner 152, and the position of the compression plate 38 with respect to the image capturing base 30.

More specifically, if the biopsy needle 50 pierces the right region of the breast 20 (see FIGS. 6A and 8A), the tilted direction determiner 154 decides that the compression plate 38 should be tilted downward to the left with respect to the image capturing base 30, whereas, if the biopsy needle 50 pierces the left region of the breast 20 (see FIGS. 7A and 9A), the tilted direction determiner 154 decides that the compression plate 38 should be tilted downward to the right with respect to the image capturing base 30. The compression plate controller 136 energizes the motor 47 according to the tilted direction, as determined by the tilted direction determiner 154, so as to tilt the compression plate 38 in the determined tilting direction.

The traveled distance calculator 156 calculates the distance by which the biopsy needle 50 moves with respect to the biopsy region 48, based on the three-dimensional position of the biopsy region 48, which has been calculated by the biopsy region position information calculator 150, the three-dimensional position of the tip end of the biopsy needle 50, which has been calculated by the biopsy needle position information calculator 134, the position of the compression plate 38, which has been calculated by the compression plate position information calculator 138 (the thickness of the breast 20), the piercing direction of the biopsy needle 50, which has been determined by the piercing direction determiner 152, and the tilted direction of the compression plate 38, which has been determined by the tilted direction determiner 154.

Based on the calculated distance by which the biopsy needle 50 is to move with respect to the biopsy region 48, the biopsy needle moving mechanism 56 moves the biopsy needle 50, in order to enable a tissue sample to be removed from the biopsy region 48 according to a lateral approach biopsy procedure.

Operations of the Mammographic Apparatus 10

The mammographic apparatus 10 according to the present embodiment is basically constructed as described above. Next, operations of the mammographic apparatus 10 will be described below with reference to the flowchart shown in FIG. 11, as well as with reference to FIGS. 1 through 10.

By way of example, the mammographic apparatus 10 performs a stereographic image capturing process after compressing the breast 20 between the image capturing base 30 and the compression plate 38, and thereafter, the mammographic apparatus 10 performs a lateral approach biopsy procedure on the breast 20 based on radiographic images generated by the stereographic image capturing process. In the flowchart shown in FIG. 11, a lateral approach biopsy procedure performed on the breast 20 after the breast 20 has been compressed and held in position will be described, first with reference to the examples shown in FIGS. 6A through 7C, and then with reference to the examples shown in FIGS. 8A through 9C.

Figure 11:
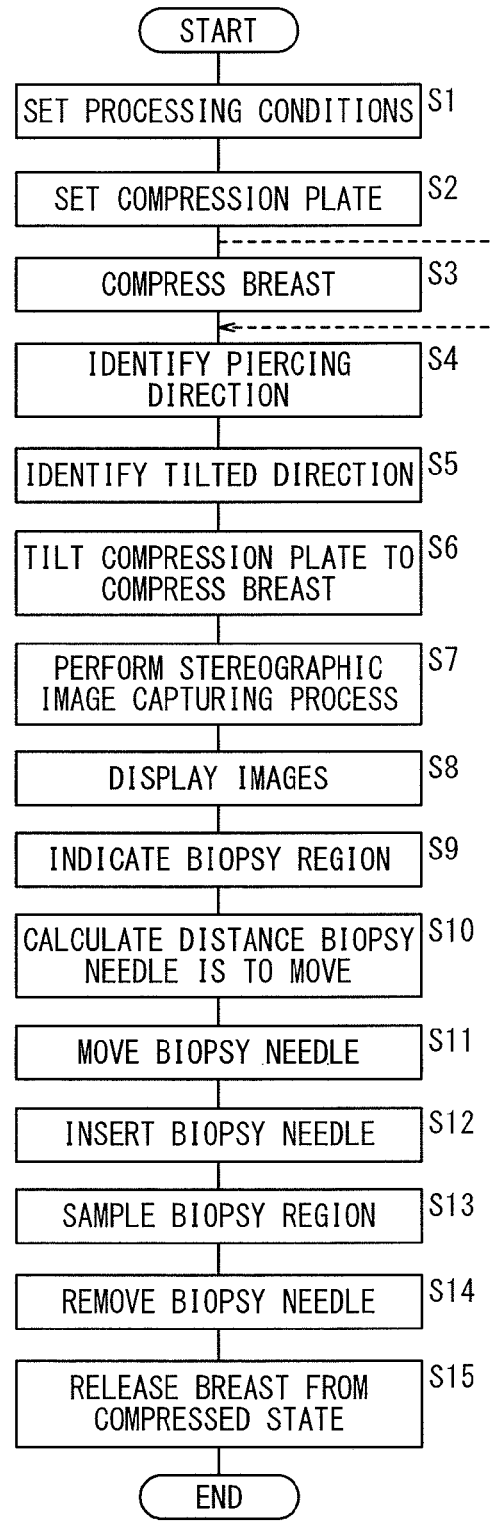
FIG. 11 is a flowchart of an operation sequence of the mammographic apparatus shown in FIG. 1.
Figure 12:
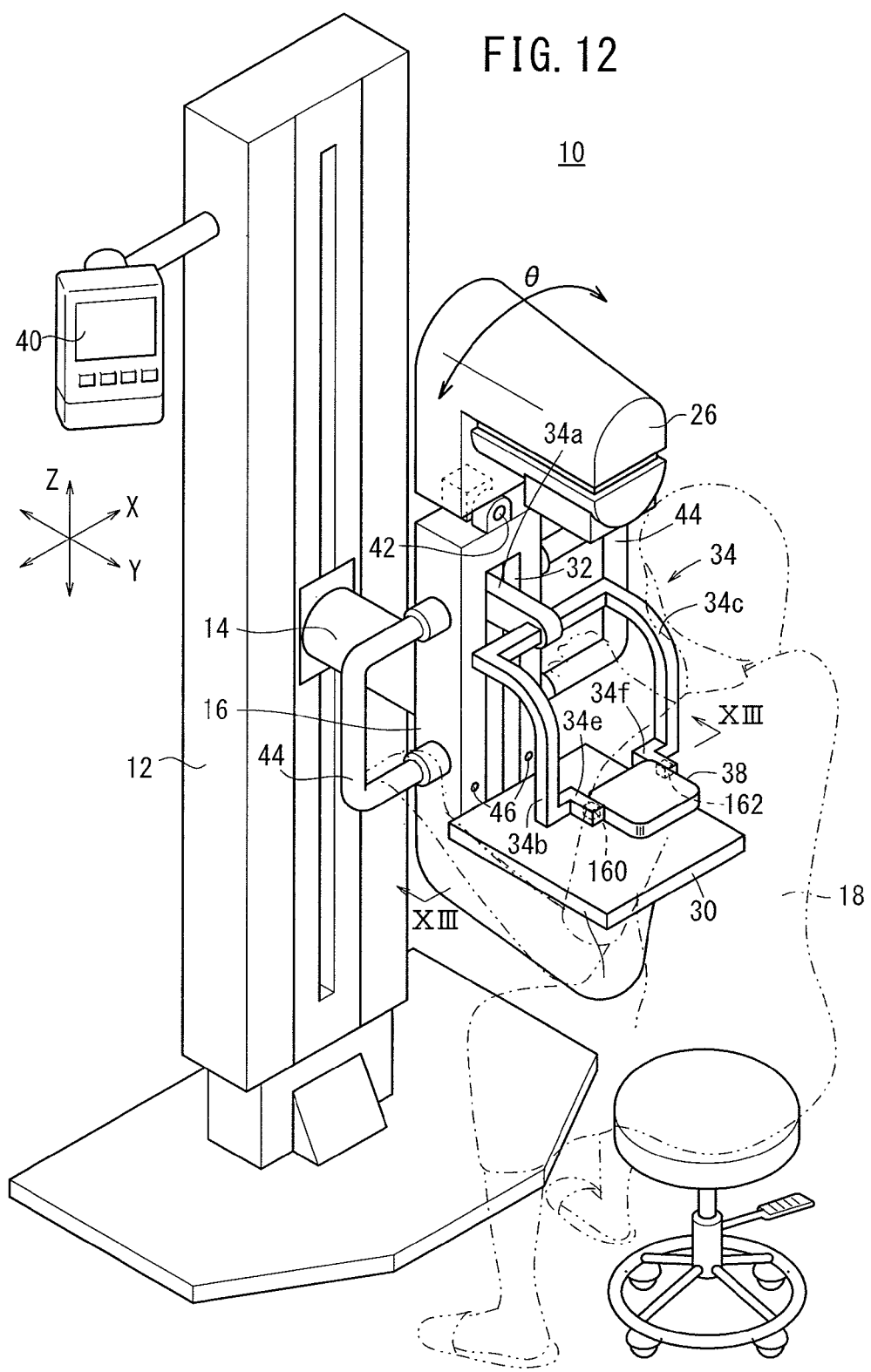
FIG. 12 is a perspective view of a mammographic apparatus according to a first modification.

In step S1 shown in FIG. 11, the image capturing condition setting section 130 (see FIG. 10) sets image capturing conditions including a tube current and a tube voltage of the radiation source 24, an irradiation dose and an irradiation time for the radiation 22, an image capturing method, and an image capturing sequence, etc., depending on characteristics of the breast 20. The image capturing conditions are set in the radiation source energization controller 132.

In step S2, the doctor or radiological technician inserts the rods 62 respectively into the holes 46 (see FIGS. 1 and 2), so as to place the biopsy apparatus 52 (see FIG. 3) including the main unit 59 in a given position on the image capturing base 30, and then inserts the proximal end portion 34a of the compression plate support 34 into the groove 32.

In step S3, the breast 20 of the examinee 18 is compressed by the image capturing base 30 and the compression plate 38. More specifically, the breast 20 is placed in a given position (i.e., at a position facing the compression plate 38) on the image capturing base 30, and then the compression plate controller 136 moves the compression plate 38, which lies parallel to the image capturing base 30, toward the image capturing base 30 in the downward direction indicated by the arrow Z, thereby compressing the breast 20. The breast 20 is compressed by the image capturing base 30 and the compression plate 38 under a uniform pressure along the directions indicated by the arrow X. The compression plate position information calculator 138 calculates the position information of the compression plate 38 with respect to the image capturing base 30.

In step S4, the biopsy needle moving mechanism 56 outputs information concerning the distance that the biopsy needle 50 is to move or turn to the biopsy needle position information calculator 134. Based on information from the biopsy needle moving mechanism 56, the biopsy needle position information calculator 134 calculates the three-dimensional position of the tip end of the biopsy needle 50. The piercing direction determiner 152 judges the piercing direction in which the biopsy needle 50 pierces the breast 20 based on the three-dimensional position of the tip end of the biopsy needle 50, which has been calculated by the biopsy needle position information calculator 134, and the position of the compression plate 38, which has been calculated by the compression plate position information calculator 138.

In step S5, the tilted direction determiner 154 determines the tilted direction in which the compression plate 38 is tilted with respect to the image capturing base 30 based on the piercing direction in which the biopsy needle 50 pierces the breast 20, which has been determined by the piercing direction determiner 152, and the position of the compression plate 38, which has been calculated by the compression plate position information calculator 138.

In step S6, the compression plate controller 136 energizes the motor 47 in accordance with the tilted direction, which was determined by the tilted direction determiner 154. The motor 47, which is energized, turns the rotational shaft 36 about its axis, thereby tilting the compression plate 38 with respect to the image capturing base 30 in the tilted direction along the directions indicated by the arrow X, whereupon the breast 20 is compressed obliquely downward by the tilted compression plate 38 and the image capturing base 30. Consequently, pressure that is applied to the breast 20 from the compression plate 38 and the image capturing base 30 is distributed unevenly along the directions indicated by the arrow X.

At this time, the breast 20, which is compressed obliquely downward, is ready to be imaged in the stereographic image capturing process.

In step S7, the mammographic apparatus 10 energizes the radiation source 24 in order to perform a stereographic image capturing process on the breast 20. More specifically, the radiation source housing unit 26 is turned about the hinge 42 (see FIG. 1) in the θ directions, so as to place the radiation source 24 successively at two different angular positions. In a case where the radiation source 24 has been placed successively at each of the two angular positions, the radiation source 24 emits radiation 22, which passes through the breast 20 and is applied to the solid-state detector 28 in the image capturing base 30. The solid-state detector 28 detects two radiographic images of the breast 20 based on radiation 22 that is transmitted through the breast 20.

The detector controller 140 controls the solid-state detector 28 so as to acquire two radiographic images of the breast 20, and then stores the acquired two radiographic images in the image information storage unit 142.

In step S8, the CAD processor 144 processes the two radiographic images, which are stored in the image information storage unit 142, and displays the processed radiographic images on the display unit 146 and the display control panel 40.

In step S9, the doctor or radiological technician selects one of a plurality of biopsy regions 48 in the two radiographic images displayed on the display unit 146 and/or the display control panel 40, from which a tissue sample is to be removed, using the biopsy region selector 148, which is a pointing device such as a mouse.

In step S10, once a desired biopsy region 48 has been selected, the biopsy region position information calculator 150 calculates the three-dimensional position of the selected biopsy region 48 based on the position of the selected biopsy region 48 in the two radiographic images. The traveled distance calculator 156 calculates the distance by which the biopsy needle 50 moves with respect to the biopsy region 48, based on the three-dimensional position of the biopsy region 48, which has been calculated by the biopsy region position information calculator 150, the three-dimensional position of the tip end of the biopsy needle 50, which has been calculated by the biopsy needle position information calculator 134, the position of the compression plate 38, which has been calculated by the compression plate position information calculator 138, the piercing direction of the biopsy needle 50, which has been determined by the piercing direction determiner 152, and the tilted direction of the compression plate 38, which has been determined by the tilted direction determiner 154.

In step S11, the biopsy needle moving mechanism 56 moves the biopsy needle 50 based on the distance, which has been calculated by the traveled distance calculator 156, by which the biopsy needle 50 moves with respect to the biopsy region 48. The biopsy needle moving mechanism 56 causes the main unit 59 thereof to control movement of the biopsy needle 50 in the directions indicated by the arrows X, Y, Z, so as to position the biopsy needle 50 in a position that faces toward the biopsy region 48, i.e., in a position facing toward the biopsy region 48 along the directions indicated by the arrow X. Then, the slider 106 is moved along the rod 98 in the directions indicated by the arrow X in order to move the biopsy needle 50 toward a side region of the breast 20. Then, in step S12, the biopsy needle 50 pierces the side region of the breast 20.

Upon the sampler 122 of the biopsy needle 50 reaching a position near the biopsy region 48, in step S13, the biopsy needle 50 starts a suction process to extract a sample tissue from the biopsy region 48 through the sampler 122. Thereafter, in step S14, the biopsy needle moving mechanism 56 retracts the biopsy needle 50 until the biopsy needle 50 is pulled out from the breast 20, whereupon the lateral approach biopsy procedure is brought to an end. Then in step S15, the compression plate 38 is elevated to release the breast 20 from the compressed state.

In this manner, the mammographic apparatus 10 operates as described above in the examples shown in FIGS. 6A through 7C.

The mammographic apparatus 10 operates in the examples shown in FIGS. 8A through 9C in the following manner. After step S2, step S3 is skipped, and steps S4, S5 are carried out.

Then, in step S6, the compression plate controller 136 energizes the motor 47 according to the tilted direction decided by the tilted direction determiner 154. The motor 47, which is energized, turns the rotational shaft 36 about its axis, thereby tilting the compression plate 38 with respect to the image capturing base 30 along the directions indicated by the arrow X, while the compression plate 38 is spaced away from the image capturing base 30.

Then, the breast 20 is compressed by the tilted compression plate 38 and the image capturing base 30. More specifically, after the breast 20 has been placed in a given position on the image capturing base 30, the compression plate controller 136 moves the compression plate 38 downwardly toward the image capturing base 30 in the direction indicated by the arrow Z, whereupon the breast 20 is compressed obliquely downward by the tilted compression plate 38 and the image capturing base 30. Consequently, pressure that is applied to the breast 20 from the compression plate 38 and the image capturing base 30 is distributed unevenly along the directions indicated by the arrow X.

Thereafter, steps S7 through S15 are carried out successively as described above.

Advantages of the Mammographic Apparatus 10

With the mammographic apparatus 10 according to the present embodiment, as described above, in a case where the breast 20 is viewed in front elevation from the chest wall 124 of the examinee 18, the compression plate 38 is tilted with respect to the image capturing base 30 along the directions indicated by the arrow X, i.e., along lateral or horizontal directions of the breast 20. At this time, the upper surface of the image capturing base 30 and the lower surface of the compression plate 38, each of which serves as a surface for compressing the breast 20, are tilted with respect to the breast 20. As a result, pressure applied to the breast 20 from the image capturing base 30 and the compression plate 38 is distributed unevenly along the directions indicated by the arrow X.

If a portion of the breast 20 where the pressure applied thereto is relatively low is pierced by the biopsy needle 50 along one of the directions indicated by the arrow X, then since the other portion of the breast 20 is compressed or held down in position under a relatively high pressure, the breast 20 is prevented from being unduly positionally displaced despite the piercing force that the breast 20 receives from the biopsy needle 50. As a consequence, the biopsy needle 50 is accurately inserted into the breast 20 with respect to the biopsy region 48, so as to enable the biopsy needle 50 to reliably and efficiently remove a sample tissue from the biopsy region 48.

According to the present embodiment, as described above, inasmuch as the compression plate 38 compresses the breast 20 while the compression plate 38 is tilted along lateral or horizontal directions, i.e., in the directions indicated by the arrow X, with respect to the image capturing base 30, pressure that is applied to the breast 20 from the image capturing base 30 and the compression plate 38 is distributed unevenly along the directions indicated by the arrow X. As a result, the compressed breast 20 is prevented from being unduly positionally displaced during the lateral approach biopsy procedure. Preventing the compressed breast 20 from being unduly positionally displaced is effective to avoid compressing the breast 20 under an excessively high pressure, so that any undue stresses on the examinee 18 and the breast 20 of the examinee 18 can be reduced.

Since the tilted direction determiner 154 determines the tilted direction in which the compression plate 38 is tilted with respect to the image capturing base 30, based on the piercing direction in which the biopsy needle 50 pieces the breast 20, as determined by the piercing direction determiner 152, the breast 20 is efficiently prevented from being unduly positionally displaced when the breast 20 is pierced by the biopsy needle 50. At this time, the tilted direction determiner 154 determines the tilted direction in which the compression plate 38 is tilted with respect to the image capturing base 30, such that the distance between the image capturing base 30 and the compression plate 38 becomes progressively smaller from one side to the other side of the breast 20. Accordingly, the pressure under which the breast 20 is compressed is relatively low on one side of the breast 20 where the compression plate 38 and the image capturing base 30 are spaced widely from each other, whereas the pressure under which the breast 20 is compressed is relatively high on the other side of the breast 20 where the compression plate 38 and the image capturing base 30 are in close proximity to each other. In a case where the one side of the breast 20 is pierced by the biopsy needle 50 along one of the directions indicated by the arrow X, since the other side of the breast 20 is compressed or held down in position under a relatively high pressure, the breast 20 is reliably prevented from being unduly positionally displaced toward the other side along the one direction indicated by the arrow X.

The piercing direction determiner 152 automatically judges the piercing direction in which the biopsy needle 50 pierces the breast 20 based on the three-dimensional position (present position) of the biopsy needle 50, which has been calculated by the biopsy needle position information calculator 134. The tilted direction determiner 154 can easily and accurately determine the tilted direction in which the compression plate 38 is tilted with respect to the image capturing base 30, based on the piercing direction as determined by the piercing direction determiner 152.

The motor 47 rotates the rotational shaft 36, which extends in the directions indicated by the arrow Y, i.e., the depth-wise direction of the breast 20, to turn the compression plate 38, thereby easily tilting the compression plate 38 with respect to the image capturing base 30.

The mammographic apparatus 10 may tilt the compression plate 38 with respect to the image capturing base 30 after the breast 20 has been compressed by the compression plate 38 and the image capturing base 30, or alternatively, may compress the breast 20 between the compression plate 38 and the image capturing base 30 after the compression plate 38 has been tilted with respect to the image capturing base 30. In either case, the breast 20 is compressed and held under an uneven pressure along the directions indicated by the arrow X.

Modifications

Modifications, i.e., first through eleventh modifications, of the present invention will be described below with reference to FIGS. 12 through 28B. Parts of the first through eleventh modifications, which are identical to those of the above embodiment shown in FIGS. 1 through 11, are denoted by identical reference characters, and such features will not be described in detail below.

FIGS. 12 through 14B show a first modification, which differs from the above embodiment (FIGS. 1 through 11), in that distal-end portions 34e, 34f extend toward the examinee 18 respectively from distal ends of the intermediate bars 34b, 34c of the compression plate support 34, and the compression plate 38 is tiltably mounted on the distal-end portions 34e, 34f.

According to the first modification, tilted state maintaining mechanisms 160, 162, which serve to tilt the compression plate 38 with respect to the image capturing base 30, and to hold or maintain the compression plate 38 tilted with respect to the image capturing base 30, are disposed between side surfaces of the distal-end portions 34e, 34f, which face toward the compression plate 38, and side surfaces of the compression plate 38, which face toward the distal-end portions 34e, 34f.

Figure 13:
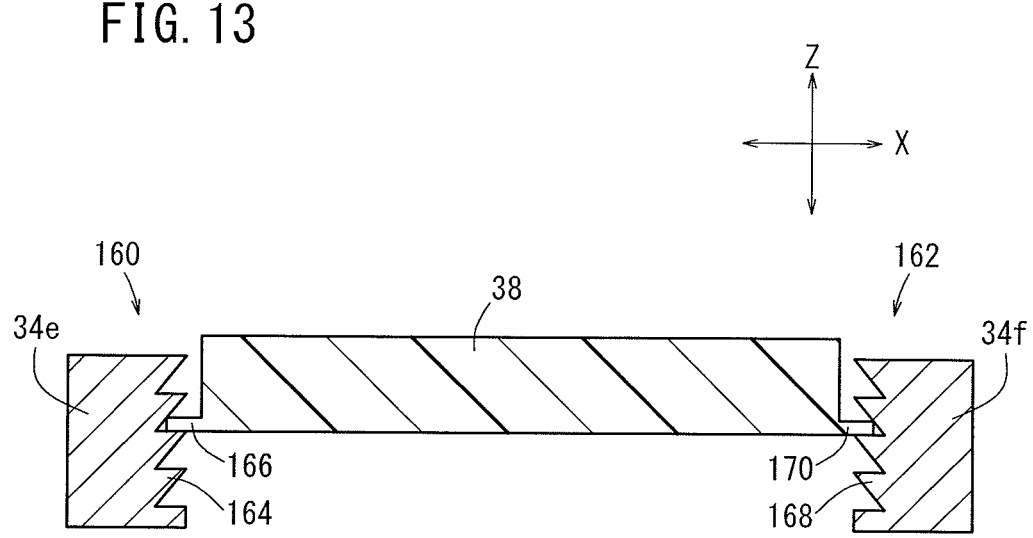
FIG. 13 is a cross-sectional view taken along line XIII-XIII of FIG. 12, showing tilted state maintaining mechanisms.

More specifically, the tilted state maintaining mechanisms 160, 162 are analogous to a lock structure of a band for fastening a plurality of cables (cable tie). As shown in FIG. 13, the tilted state maintaining mechanisms 160, 162 have respective sets of engaging grooves 164, 168 disposed on respective side surfaces of the distal-end portions 34e, 34f, which face toward the compression plate 38 and are arrayed along the directions indicated by the arrow Z, and respective fingers 166, 170 disposed on respective side surfaces of the compression plate 38 for engagement in selected ones of the engaging grooves 164, 168.

Each of the engaging grooves 164, 168 is defined by a tapered surface, which is inclined obliquely downward, and a horizontal surface that extends in the directions indicated by the arrow X. The fingers 166, 170 can be held on the respective horizontal surfaces. The fingers 166, 170 have a length, which is large enough to be held on the horizontal surfaces of the engaging grooves 164, 168, and a thickness, which is sufficiently smaller than the compression plate 38, so as to enable the fingers 166, 170 to be flexible.

According to the first modification, as shown in FIG. 13, for maintaining the compression plate 38 along the directions indicated by the arrow X in parallel with the image capturing base 30, the fingers 166, 170 engage within the horizontal surfaces of certain engaging grooves 164, 168, which are at the same height.

Figure 14A:
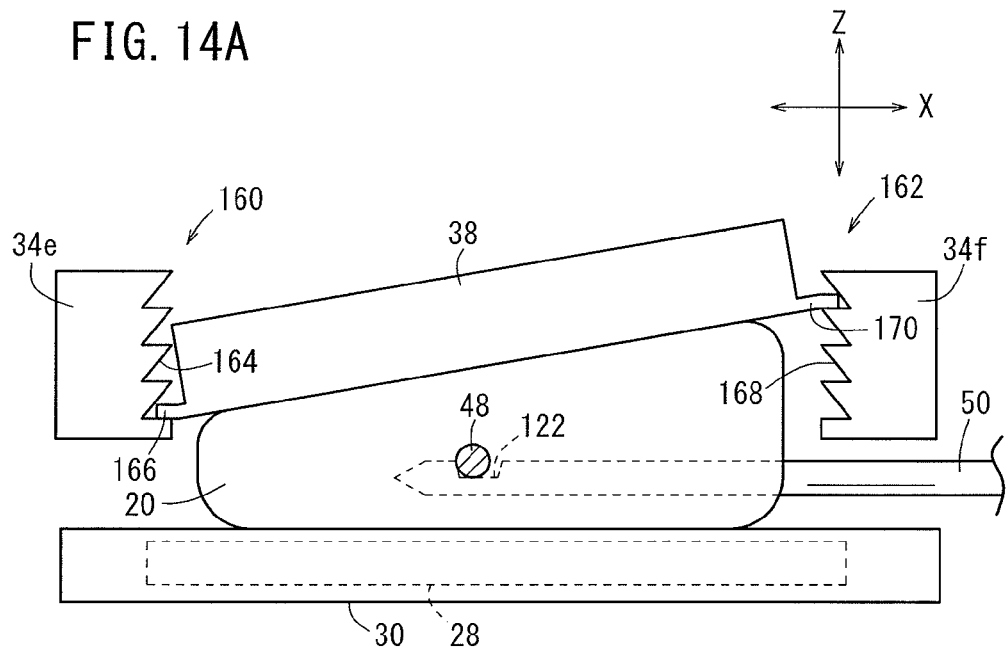
FIGS. 14A and 14B are front elevational views showing the manner in which a biopsy needle is inserted into a breast, which is compressed by tilted compression plates and an image capturing base according to the first modification.

For tilting the compression plate 38 downward to the left in FIG. 14A with respect to the image capturing base 30, the doctor or radiological technician presses the left side of the compression plate 38 toward the image capturing base 30. Under such an applied pressing force, a distal end of the flexible finger 166 is curved upwardly along the tapered surface toward the compression plate 38 about the proximal end thereof, which is joined to the compression plate 38. The finger 166 then is released out of engagement with the engaging groove 164, thereby allowing the left side of the compression plate 38 to descend toward the image capturing base 30 under the pressing force.

As a result, the finger 166 is taken out from the engaging groove 164 and is inserted into the next lower engaging groove 164. Immediately thereafter, the finger 166 snaps out of the curved state, whereby the distal end of the finger 166 moves along the tapered surface of the next lower engaging groove 164 about the proximal end thereof, until the finger 166 hits against the horizontal surface of the next lower engaging groove 164. Upon the finger 166 hitting against the horizontal surface of the next lower engaging groove 164, the finger 166 is held in the next lower engaging groove 164. As a result, the compression plate 38 is tilted downward to the left in FIG. 14A, and is maintained in such a tilted state.

FIG. 14A shows the finger 166, which engages in the lowermost engaging groove 164 of the distal-end portion 34e. In order to bring the finger 166 into engagement with the lowermost engaging groove 164, the doctor or radiological technician continuously presses the left side of the compression plate 38, so as to angularly displace the compression plate 38 from the horizontal state shown in FIG. 13 to the tilted state shown in FIG. 14A.

Figure 14B:
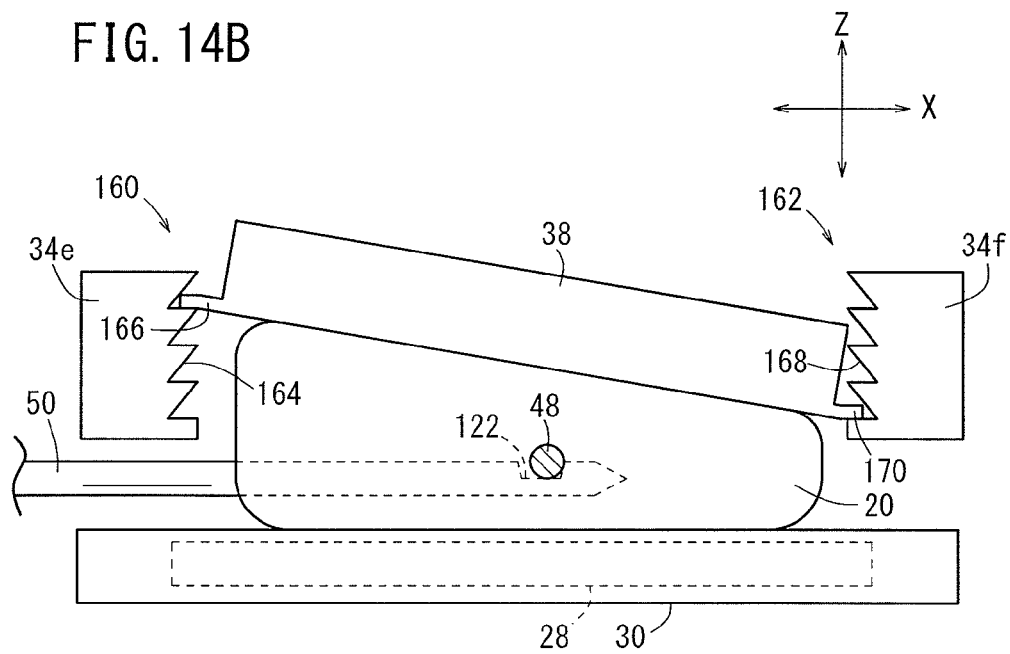
Figure 15:
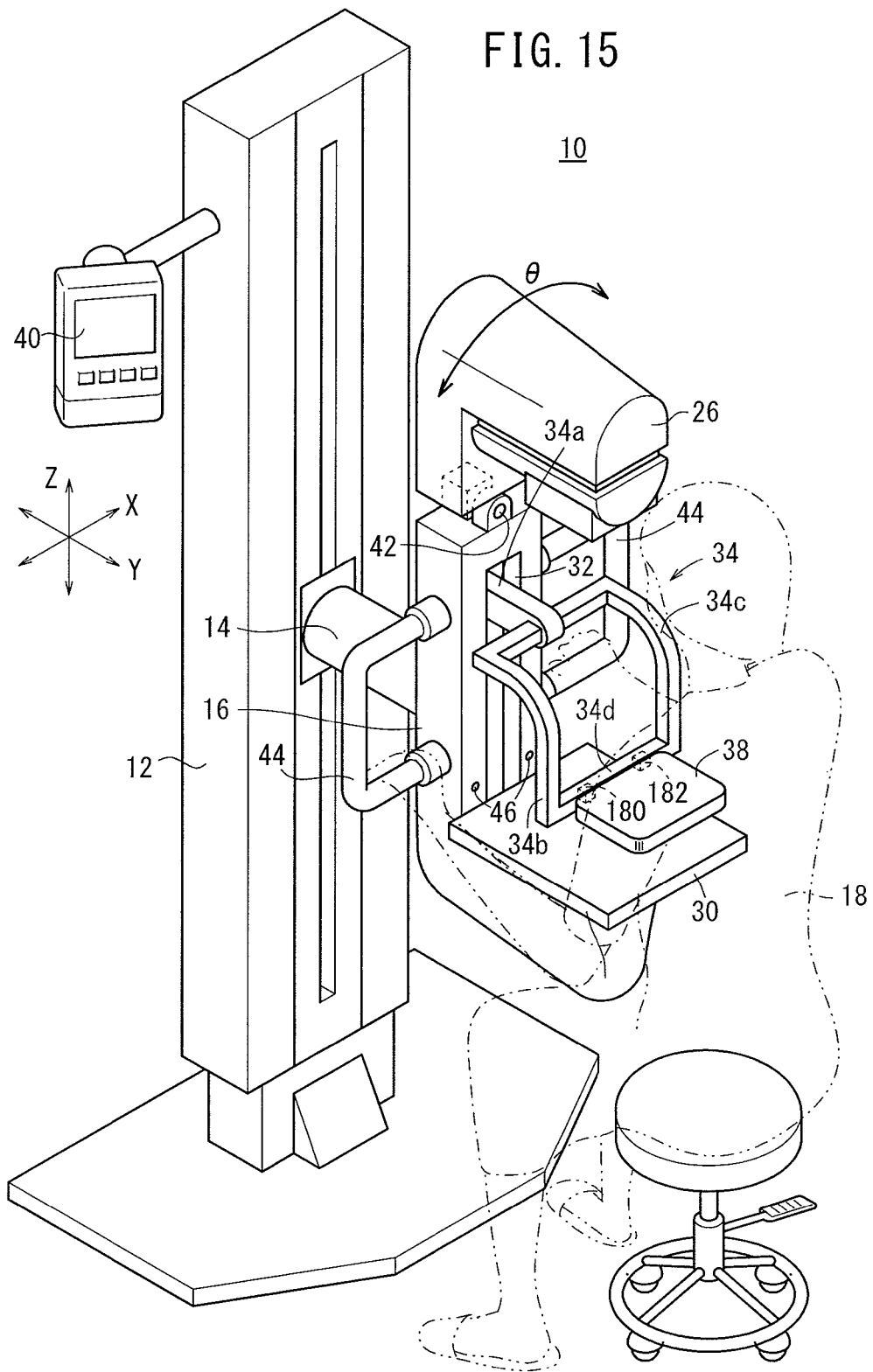
FIG. 15 is a perspective view of a mammographic apparatus according to a second modification.

FIG. 14B shows the finger 170, which engages in the lowermost engaging groove 168 of the distal-end portion 34f. In order to bring the finger 170 into engagement with the lowermost engaging groove 168, the doctor or radiological technician continuously presses the right side of the compression plate 38, so as to angularly displace the compression plate 38 from the horizontal state shown in FIG. 13 to the tilted state shown in FIG. 14B.

According to the first modification, because the compression plate 38 can be tilted with respect to the image capturing base 30, the advantages of the above embodiment can easily be achieved. Furthermore, since the compression plate 38 can be maintained in a tilted state by the tilted state maintaining mechanisms 160, 162, the breast 20 can reliably be kept in a compressed state.

In the first modification, the doctor or radiological technician presses the right or left side of the compression plate 38 from above in order to tilt the compression plate 38 downward to the right or left with respect to the image capturing base 30. However, a pressing mechanism (not shown) may also be used to automatically press the compression plate 38.

The tilted direction, which is determined by the tilted direction determiner 154, preferably is displayed on the display unit 146 and/or the display control panel 40. By observing the displayed tilted direction, the doctor or radiological technician can easily recognize the region (right or left side) of the compression plate 38 that is to be pressed, and hence can easily and accurately carry out the process of tilting the compression plate 38.

Each of the engaging grooves 164, 168 is defined by a tapered surface, which extends from the horizontal surface upwardly toward the side surface of the compression plate 38. Therefore, although the fingers 166, 170 can be lowered toward the image capturing base 30, the fingers 166, 170 are prevented from moving upwardly by the tapered surfaces. For elevating the compression plate 38, the doctor or radiological technician may use a pin (not shown) in order to curve the tip ends of the fingers 166, 170 toward the compression plate 38, whereupon the compression plate 38 can be moved to a desired height.

FIGS. 15 through 17B show a second modification, which differs from the above embodiment (FIGS. 1 through 11) and the first modification (FIGS. 12 through 14B), in that the compression plate 38 is tiltably mounted on the joint 34d by tilted state maintaining mechanisms 180, 182, which are disposed between the joint 34d of the compression plate support 34 and a side surface of the compression plate 38 that faces toward the joint 34d.

More specifically, a side surface of the joint 34d, which faces toward the compression plate 38, i.e., which confronts the chest wall 124 of the examinee 18, has two holes 184, 194 defined therein for receiving respective arms 188, 198 that extend respectively from left and right sides of the compression plate 38 toward the joint 34d. The holes 184, 194 include respective sets of engaging grooves 186, 196 provided in respective outer side surfaces that partially define the holes 184, 194, and which are arrayed along the directions indicated by the arrow Z. The arms 188, 198 have respective fingers 190, 200, which are engageable in selected ones of the engaging grooves 186, 196.

The fingers 190, 200 and the engaging grooves 186, 196 jointly make up the tilted state maintaining mechanisms 180, 182, respectively. The tilted state maintaining mechanisms 180, 182 possess substantially the same functions as the tilted state maintaining mechanisms 160, 162 according to the first modification.

More specifically, each of the engaging grooves 186, 196 is defined by a tapered surface, which is inclined obliquely downward, and a horizontal surface extending in the directions indicated by the arrow X, such that the fingers 190, 200 are capable of being held on the respective horizontal surfaces. The fingers 190, 200 have a length large enough to be held on the horizontal surfaces of the engaging grooves 186, 196, and a thickness that is sufficiently smaller than the arms 188, 198 so as to enable the fingers 190, 200 to be flexible.

Figure 16:
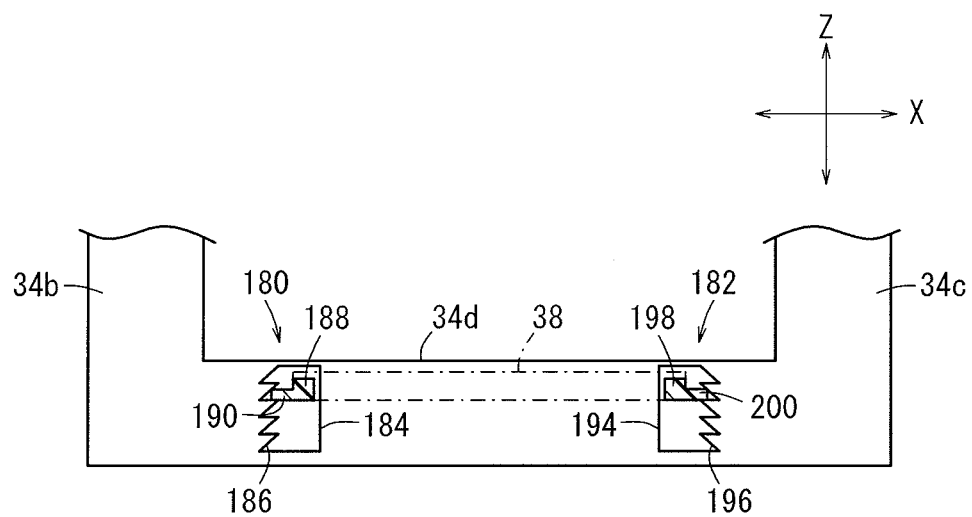
FIG. 16 is a fragmentary front elevational view of tilted state maintaining mechanisms according to the second modification.

According to the second modification, for maintaining the compression plate 38 parallel to the image capturing base 30 along the directions indicated by the arrow X, the arms 188, 198 are inserted into the respective holes 184, 194, whereupon the fingers 190, 200 come into engagement with the horizontal surfaces of the engaging grooves 186, 196, which are at the same height, as shown in FIG. 16. The compression plate 38 and the joint 34*d* have retaining mechanisms (not shown) for retaining the arms 188, 198 in the holes 184, 194, and for preventing removal thereof in a case where the arms 188, 198 have been inserted into the holes 184, 194 to install the compression plate 38 on the compression plate support 34.

Figure 17A:
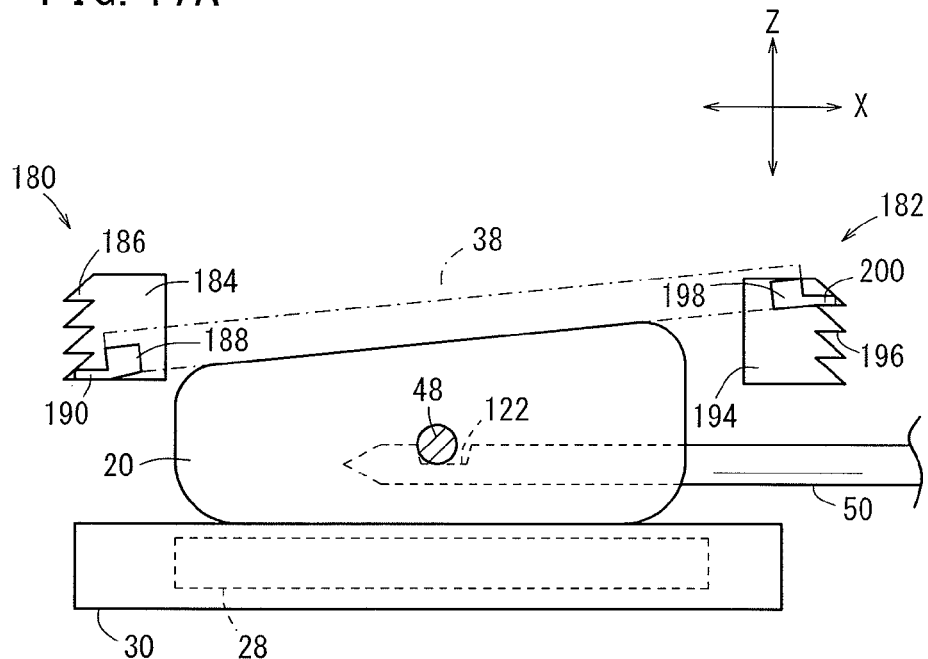
FIGS. 17A and 17B are front elevational views showing the manner in which a biopsy needle is inserted into a breast, which is compressed by tilted compression plates and an image capturing base according to the second modification.

For tilting the compression plate 38 downward to the left in FIG. 17A with respect to the image capturing base 30, the doctor or radiological technician presses the left side of the compression plate 38 toward the image capturing base 30. Under such an applied pressing force, a distal end of the flexible finger 190 is curved upwardly along the tapered surface toward the compression plate 38 about the proximal end thereof, which is joined to the arm 188 of the compression plate 38. At this time, the finger 190 is released from engagement with the engaging groove 186, thereby allowing the left side of the compression plate 38 to descend toward the image capturing base 30 under the pressing force.

As a result, the finger 190 is taken out from the engaging groove 186 and is placed in the next lower engaging groove 186. Immediately thereafter, the finger 190 snaps out of the curved state, whereupon the distal end of the finger 190 moves along the tapered surface of the next lower engaging groove 186 about the proximal end thereof, until the finger 190 comes into abutment against the horizontal surface of the next lower engaging groove 186. In a case where the finger 190 abuts against the horizontal surface of the next lower engaging groove 186, the finger 190 is held in the next lower engaging groove 186. As a result, the compression plate 38 is tilted downward to the left in FIG. 17A, and is maintained in the tilted state.

In FIG. 17A, the doctor or radiological technician may continuously press the left side of the compression plate 38 so as to angularly displace the compression plate 38 from the horizontal state shown in FIG. 16 to the tilted state shown in FIG. 17A.

Figure 17B:
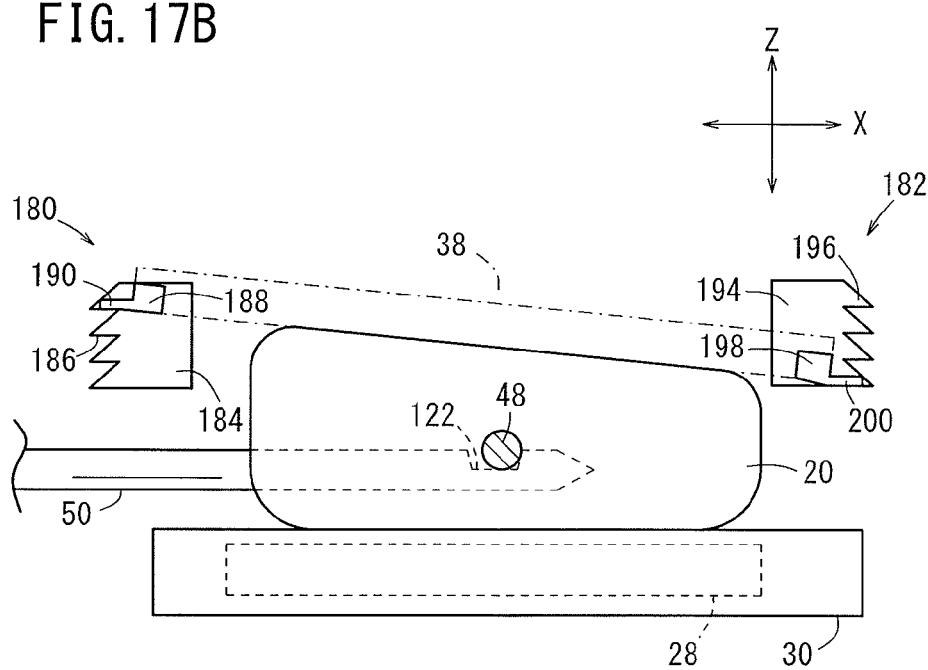

FIG. 17B shows the finger 200, which engages in the lowermost engaging groove 196 of the hole 194. In order to bring the finger 200 into engagement with the lowermost engaging groove 196, the doctor or radiological technician continuously presses the right side of the compression plate 38, so as to angularly displace the compression plate 38 from the horizontal state shown in FIG. 16 to the tilted state shown in FIG. 17B.

According to the second modification, the advantages of the above embodiment and the first modification can easily be achieved, because the compression plate 38 is capable of being tilted with respect to the image capturing base 30. According to the second modification, as with the first modification, pressing mechanisms (not shown) may be used to automatically press the compression plate 38. Further, the tilted direction, which is determined by the tilted direction determiner 154, may be displayed on the display unit 146 and/or the display control panel 40, and the doctor or radiological technician may use a pin (not shown) in order to move the compression plate 38 to a desired height.

Figure 18A:
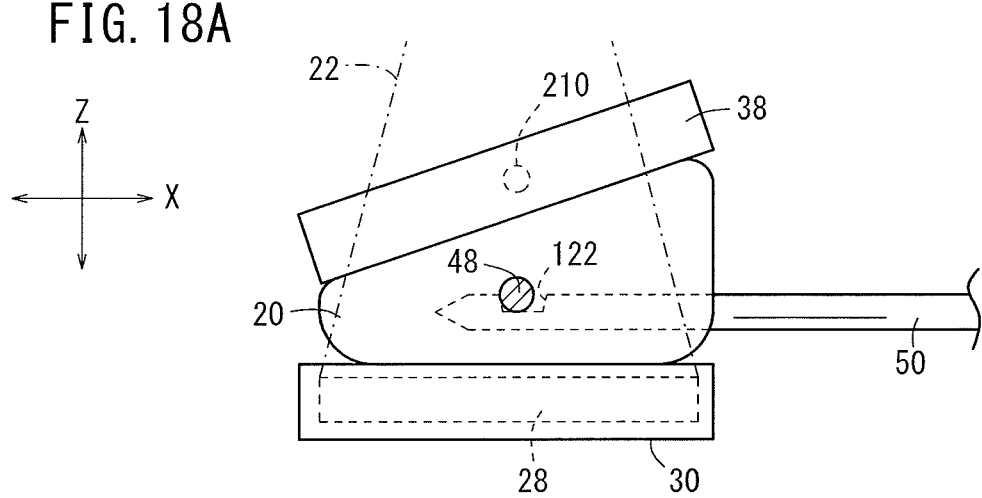
FIGS. 18A and 18B are front elevational views showing the manner in which a biopsy needle is inserted into a breast, which is compressed by a tilted compression plate and an image capturing base according to a third modification.
Figure 18B:
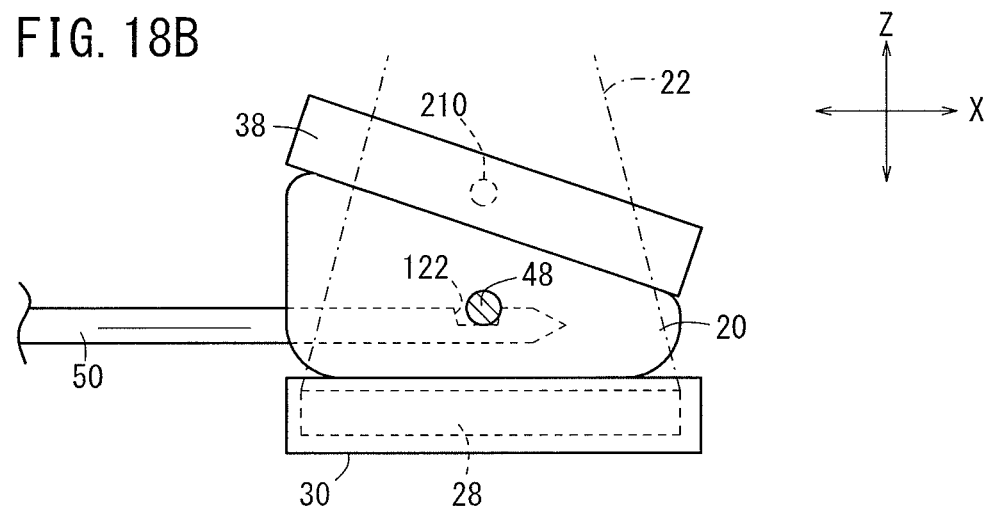

FIGS. 18A and 18B show a third modification, which differs from the above embodiment (FIGS. 1 through 11) and the first and second modifications (FIGS. 12 through 17B), in that the compression plate 38 is coupled to the compression plate support 34 by a shaft 210. According to the third modification, the biopsy apparatus is free of the rotational shaft 36 and the motor 47. The compression plate 38 is coupled to the compression plate support 34 by the shaft 210, while the compression plate 38 is tilted downward to the left or right along the directions indicated by the arrow X with respect to the image capturing base 30.

The third modification offers the same advantages as the above embodiment, because the breast 20 is compressed and held by the tilted compression plate 38 and the image capturing base 30.

FIGS. 19A and 19B show a fourth modification, which differs from the third modification (FIGS. 18A and 18B), in that a lower surface 212 of the compression plate 38 is constructed as a slanted surface, which is inclined with respect to the image capturing base 30. If the compression plate 38 is lowered toward the image capturing base 30, the breast 20 is obliquely compressed and held by the upper surface of the image capturing base 30 and the slanted lower surface 212 of the compression plate 38, which is tilted with respect to the image capturing base 30.

As described above, the lower surface 212 of the compression plate 38 is constructed as a slanted surface, which is inclined with respect to the image capturing base 30, thereby keeping the compression plate 38 tilted with respect to the upper surface of the image capturing base 30. Therefore, simply by the compression plate 38 being displaced toward the image capturing base 30, the breast 20 is compressed and held under an uneven pressure along the directions indicated by the arrow X. As a result, the fourth modification offers the same advantages as the above embodiment and the first through third modifications.

Figure 20A:
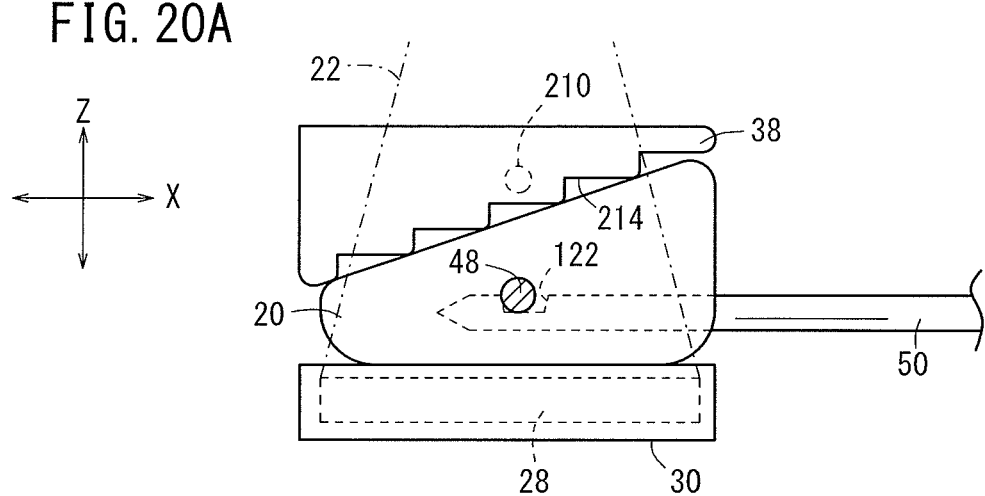
FIGS. 20A and 20B are front elevational views showing the manner in which a biopsy needle is inserted into a breast, which is compressed by a slanted surface of a compression plate and an image capturing base according to a fifth modification.
Figure 20B:
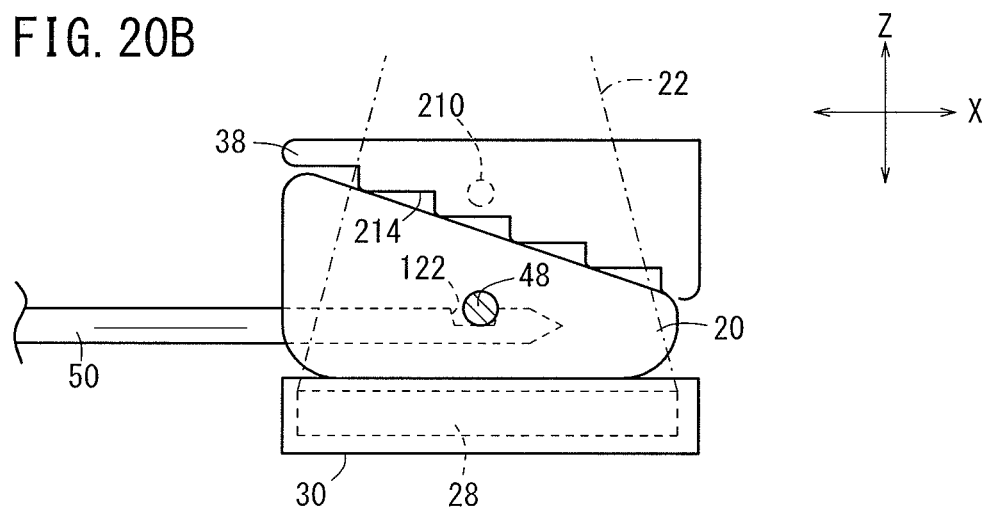

FIGS. 20A and 20B show a fifth modification, which differs from the fourth modification (FIGS. 19A and 19B), in that the compression plate 38 has a lower surface 214 constructed as a stepped slanted surface. Inasmuch as the lower surface 214 of the compression plate 38 is constructed as a slanted surface inclined with respect to the image capturing base 30, simply by the compression plate 38 being displaced toward the image capturing base 30, the breast 20 is compressed and held under an uneven pressure along the directions indicated by the arrow X.

Figure 21A:
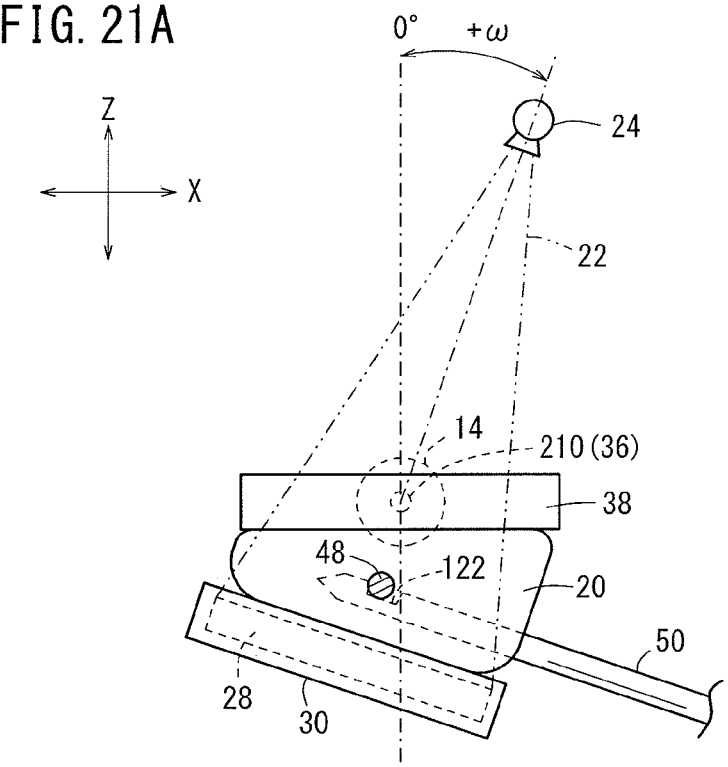
FIGS. 21A and 21B are front elevational views showing the manner in which a biopsy needle is inserted into a breast, which is compressed by a compression plate and an image capturing base while the image capturing base and a radiation source are turned or tilted with respect to the compression plate according to a sixth modification.
Figure 21B:
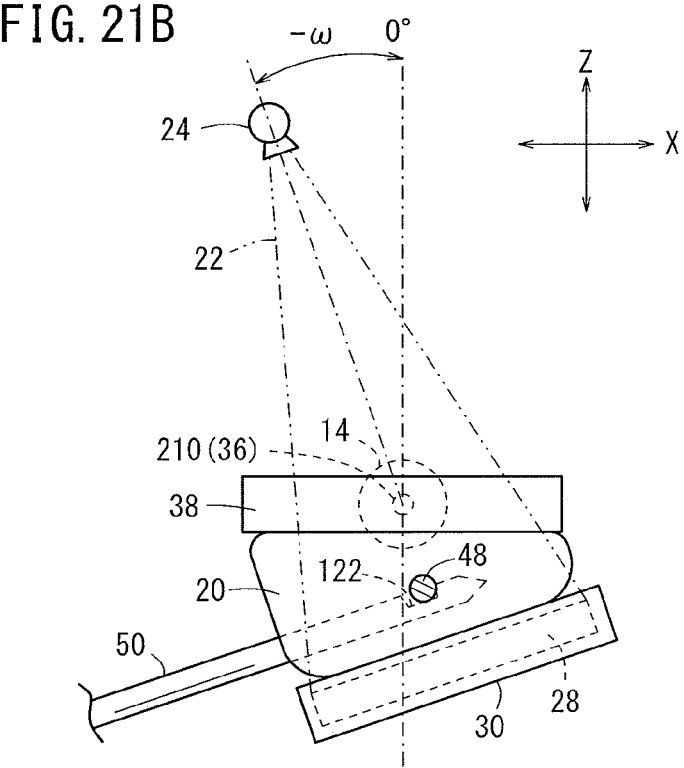

FIGS. 21A and 21B show a sixth modification, which differs from the above embodiment (FIGS. 1 through 11) as well as the first through fifth modifications (FIGS. 12 through 20B), in that the arm 16 is turned about the swing shaft 14 in order to tilt the radiation source housing unit 26, which houses the radiation source 24 therein, and the image capturing base 30 with respect to the compression plate 38.

The compression plate 38 is tiltably coupled to the compression plate support 34 by the rotational shaft 36, or alternatively, the compression plate 38 is coupled to the compression plate support 34 by the shaft 210 while the compression plate 38 is tilted.

According to the tilted direction, which is determined by the tilted direction determiner 154, the arm 16 is turned about the swing shaft 14 so as to turn the radiation source 24 and the image capturing base 30 from a position $\omega = 0°$, i.e., a vertical position along the directions indicated by the arrow Z, through an angle of $-\omega$ or $+\omega$. The motor 47 is energized to turn the rotational shaft 36, so as to keep the compression plate 38 substantially horizontal along the directions indicated by the arrow X. Therefore, the image capturing base 30 is tilted with respect to the compression plate 38.

If the compression plate 38 is coupled to the compression plate support 34 by the shaft 210 while the compression plate 38 is tilted, then in accordance with the tilted direction determined by the tilted direction determiner 154, the arm 16 is turned about the swing shaft 14 in order to turn the radiation source 24 and the image capturing base 30 through an angle of −ω or +ω. At this time, the compression plate 38 lies substantially horizontally along the directions indicated by the arrow X, and therefore, the image capturing base 30 is tilted with respect to the compression plate 38.

In any case, since the image capturing base 30 is tilted with respect to the compression plate 38, the breast 20 is compressed and held under an uneven pressure along the directions indicated by the arrow X. As a result, the sixth modification offers the same advantages as the above embodiment and the first through fifth modifications.

Figure 22A:
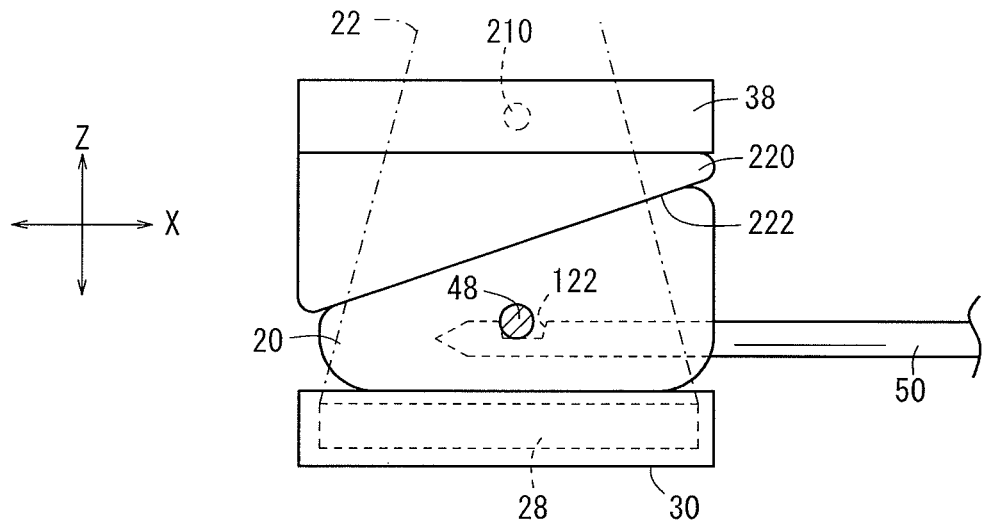
FIGS. 22A and 22B are front elevational views showing the manner in which a biopsy needle is inserted into a breast, which is compressed by a slanted surface of a spacer on a compression plate and an image capturing base according to a seventh modification.
Figure 22B:
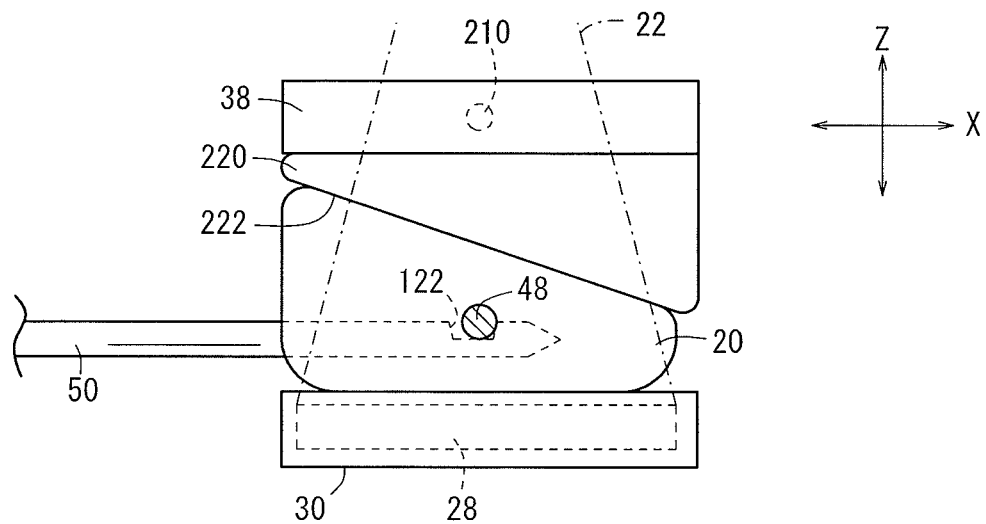

FIGS. 22A and 22B show a seventh modification, which differs from the above embodiment (FIGS. 1 through 11) and the first through sixth modifications (FIGS. 12 through 21B), in that a spacer 220 (first spacer) is disposed on a side surface of the compression plate 38 to face toward the breast 20, and has a lower surface 222 constructed as a slanted surface, which is inclined with respect to the image capturing base 30.

If the compression plate 38 and the spacer 220 are lowered toward the image capturing base 30, the breast 20 is compressed obliquely and held between the upper surface of the image capturing base 30 and the slanted lower surface 222 of the spacer 220.

As described above, the lower surface 222 of the spacer 220 is constructed as a slanted surface, which is inclined with respect to the image capturing base 30, thereby keeping the spacer 220 tilted with respect to the upper surface of the image capturing base 30. Therefore, simply by displacing the compression plate 38 and the spacer 220 toward the image capturing base 30, the breast 20 is compressed and held under an uneven pressure along the directions indicated by the arrow X. As a result, the seventh modification offers the same advantages as the above embodiment and the first through fifth modifications.

Figure 23A:
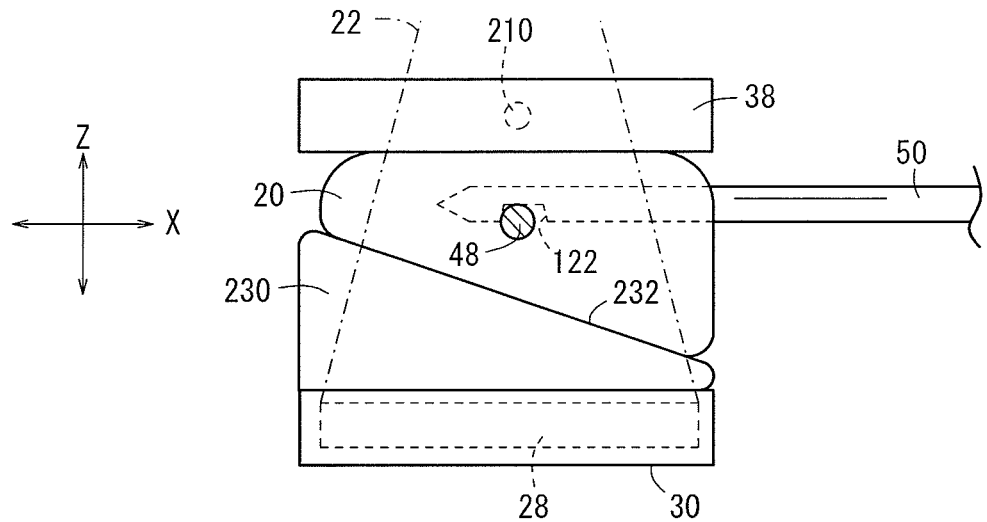
FIGS. 23A and 23B are front elevational views showing the manner in which a biopsy needle is inserted into a breast, which is compressed by a slanted surface of a spacer on an image capturing base and a compression plate according to an eighth modification.
Figure 23B:
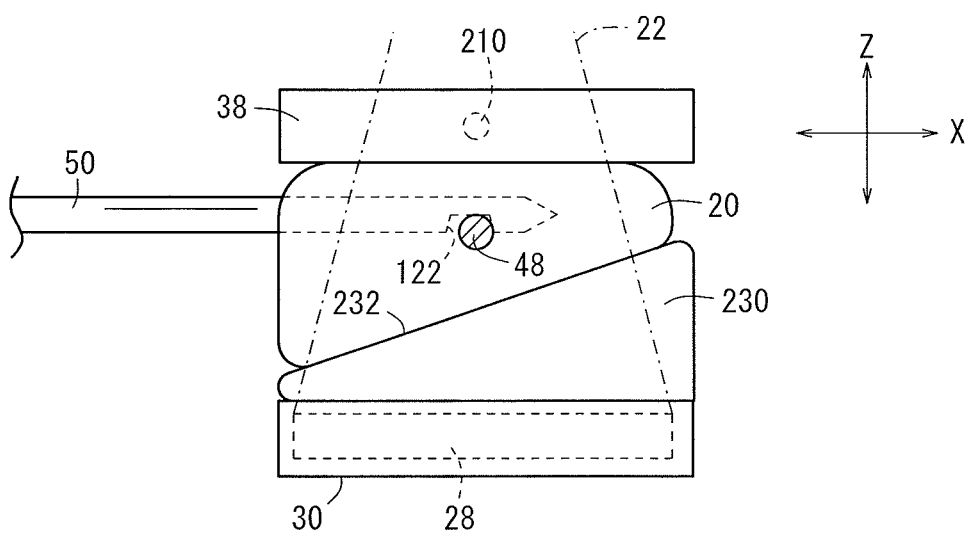
Figure 24:
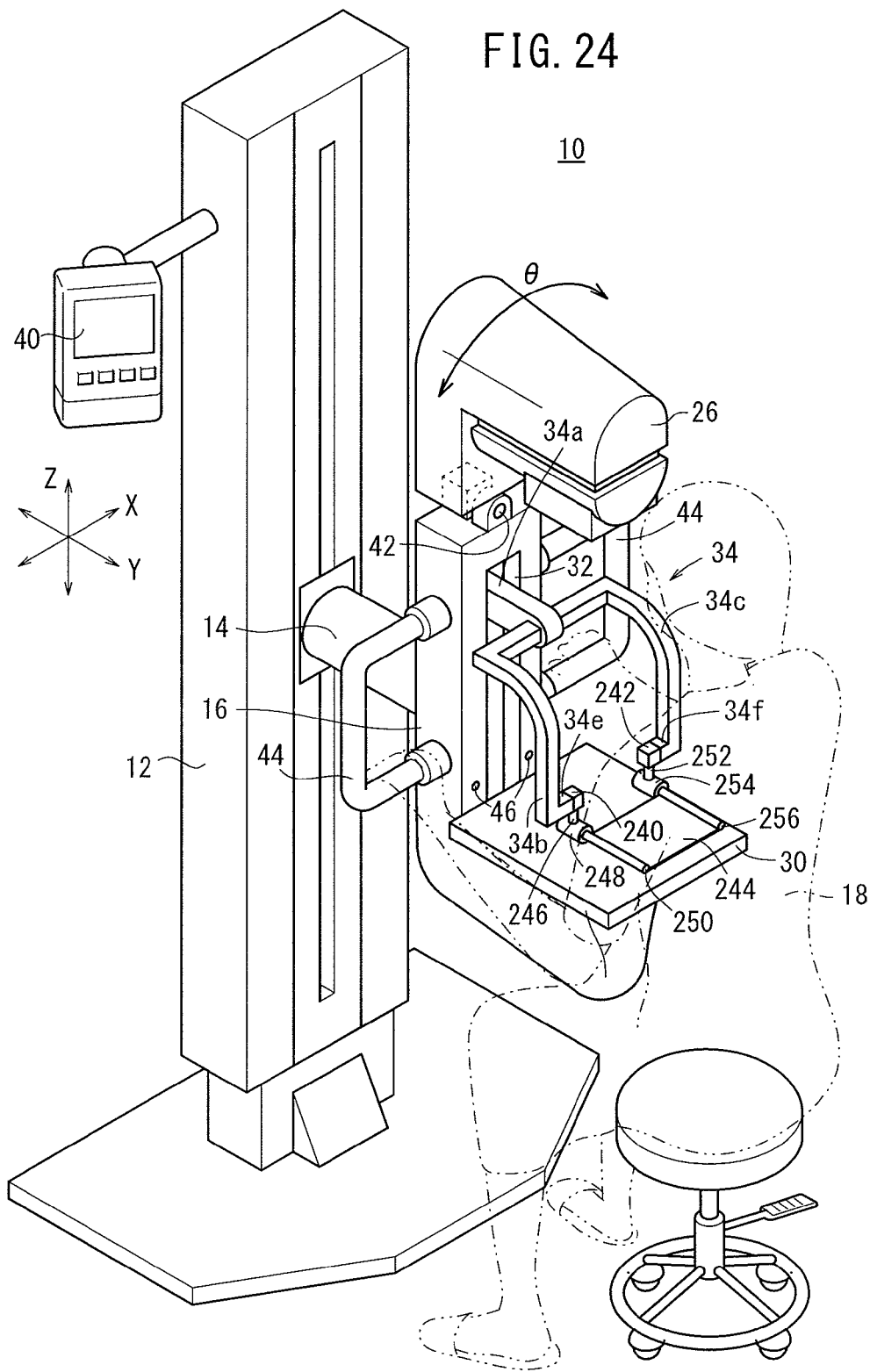
FIG. 24 is a perspective view of a mammographic apparatus according to a ninth modification.

FIGS. 23A and 23B show an eighth modification, which differs from the seventh modification (FIGS. 22A and 22B), in that a spacer 230 (second spacer) is disposed on an upper surface of the image capturing base 30 that faces toward the breast 20. The spacer 230 has an upper surface 232 constructed as a slanted surface, which is inclined with respect to the compression plate 38.

If the compression plate 38 is lowered toward the spacer 230 and the image capturing base 30, the breast 20 is obliquely compressed and held by the upper surface 232 of the spacer 230 and the compression plate 38.

As described above, the upper surface 232 of the spacer 230 is constructed as a slanted surface, which is inclined with respect to the compression plate 38, thereby keeping the spacer 230 tilted with respect to the compression plate 38. Therefore, simply by displacing the compression plate 38 toward the spacer 230 and the image capturing base 30, the breast 20 is compressed and held under an uneven pressure along the directions indicated by the arrow X. As a result, the eighth modification offers the same advantages as the above embodiment and the first through seventh modifications.

FIGS. 24 through 26B show a ninth modification, which differs from the above embodiment (FIGS. 1 through 11) and the first through eighth modifications (FIGS. 12 through 23B), in that motor-driven cylinders 240, 242 (first and second rod movement controllers) are mounted respectively on the distal-end portions 34e, 34f of the compression plate support 34. Respective rods 246, 252 of the motor-driven cylinders 240, 242 are moved toward and away from the image capturing base 30. Further, in a case where the motor-driven cylinders 240, 242 are operated to move the respective rods 246, 252 toward the image capturing base 30 in a downward direction as indicated by the arrow Z, the rods 246, 252 displace a flexible compression sheet 244 (compression member), which is made of resin, toward the image capturing base 30.

Tubular members 248, 254 are fixed to distal ends of the respective rods 246, 252 of the motor-driven cylinders 240, 242, and rods 250, 256 (first and second rods) extend from the respective tubular members 248, 254 toward the examinee 18. Lateral opposite ends of the compression sheet 244 are spaced from each other along the directions indicated by the arrow X, and are supported respectively by the rods 250, 256.

Figure 25A:
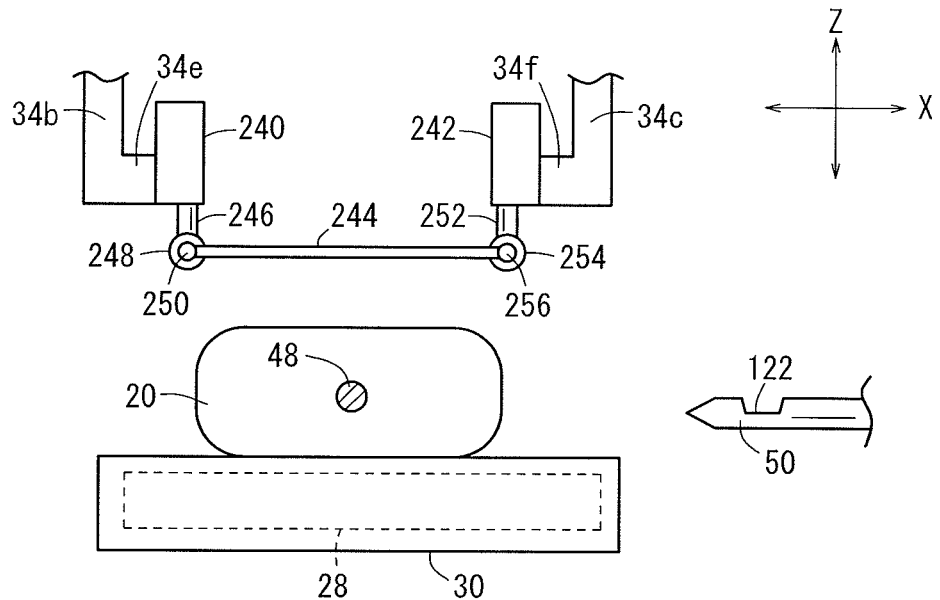
FIG. 25A is a front elevational view showing a breast prior to being compressed by a compression sheet and an image capturing base of the mammographic apparatus shown in FIG. 24.

In a case where the compression sheet 244 is spaced by a wide margin from the breast 20 and the image capturing base 30, as shown in FIG. 25A, the respective rods 246, 252 of the motor-driven cylinders 240, 242 are retracted to the same height above the image capturing base 30. The rods 250, 256, which are connected to the rods 246, 252 by the respective tubular members 248, 254, also are retracted to the same height above the image capturing base 30. At this time, the compression sheet 244 lies substantially parallel to the image capturing base 30 along the directions indicated by the arrow X.

For compressing and holding the breast 20 with the compression sheet 244 and the image capturing base 30, the motor-driven cylinders 240, 242 are actuated to displace the respective rods 246, 252 toward the image capturing base 30 by different distances. For example, as shown in FIG. 25B, if the distance that the rod 246 is moved is greater than the distance that the rod 252 is moved by ΔZ, then the tubular member 248 and the rod 250 are lowered toward the image capturing base 30 by a greater distance ΔZ than the tubular member 254 and the rod 256.

Figure 25B:
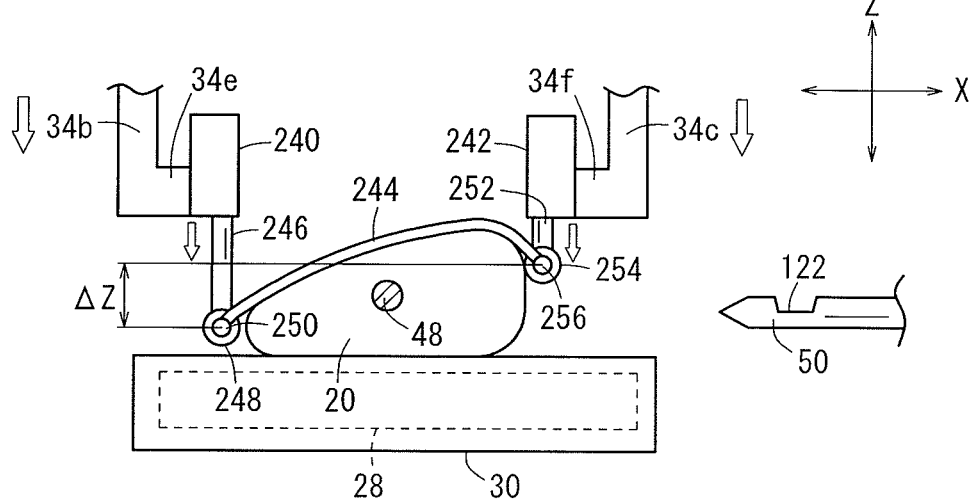
FIG. 25B is a front elevational view showing a breast, which is compressed and held in position by the compression sheet and the image capturing base of the mammographic apparatus shown in FIG. 24.
Figure 26A:
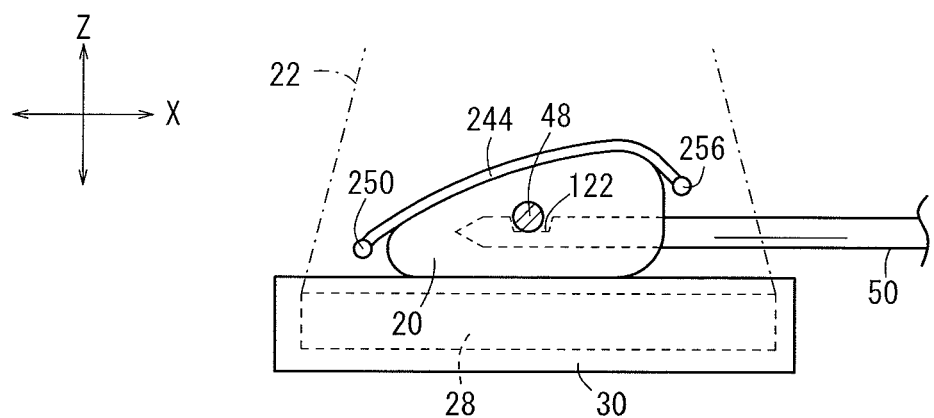
FIGS. 26A and 26B are front elevational view showing the manner in which a biopsy needle is inserted into a breast, which is compressed and held in position by the compression sheet and the image capturing base of the mammographic apparatus shown in FIG. 24.

Therefore, the compression sheet 244, which is supported by the rods 250, 256, is tilted downward to the left in FIGS. 25B and 26A with respect to the image capturing base 30 while covering the upper portion of the breast 20. As a result, the breast 20 is compressed and held by the tilted compression sheet 244 and the image capturing base 30 under an uneven pressure along the directions indicated by the arrow X.

Figure 26B:
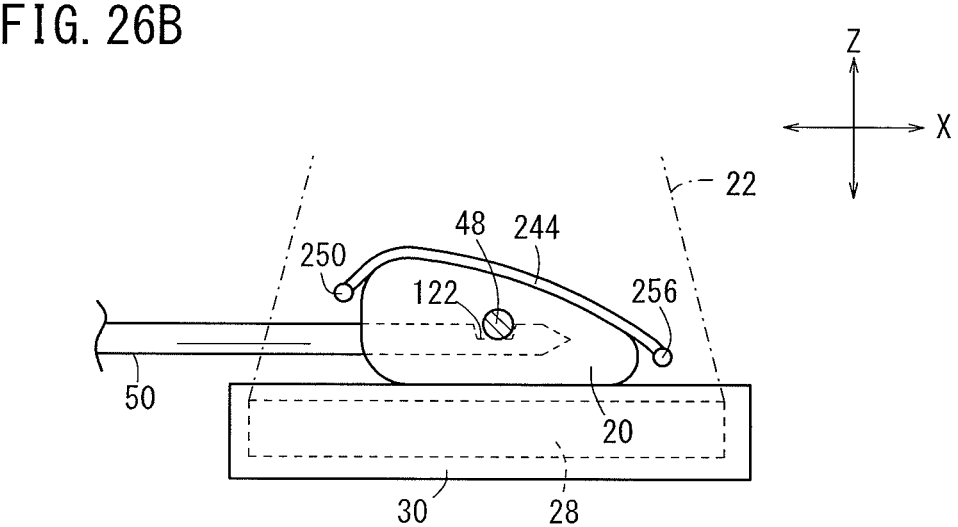

FIGS. 25B and 26A illustrate that the compression sheet 244 compresses and holds the breast 20 while the compression sheet 244 is tilted downward to the left with respect to the image capturing base 30. On the other hand, FIG. 26B illustrates that the compression sheet 244 compresses and holds the breast 20 while the compression sheet 244 is tilted downward to the right with respect to the image capturing base 30. In FIG. 26B, the distance that the rod 252 moves is greater than the distance that the rod 246 moves, thereby tilting the compression sheet 244 downward to the right while the tilted compression sheet 244 compresses and holds the breast 20.

According to the ninth embodiment, the compression sheet 244 is tilted with respect to the image capturing base 30 in a case where the motor-driven cylinders 240, 242 are operated to move the rods 250, 256 by different distances toward the image capturing base 30. Consequently, the breast 20 is compressed and held under an uneven pressure along the directions indicated by the arrow X. As a result, the ninth modification offers the same advantages as the above embodiment and the first through eighth modifications.

Figure 27A:
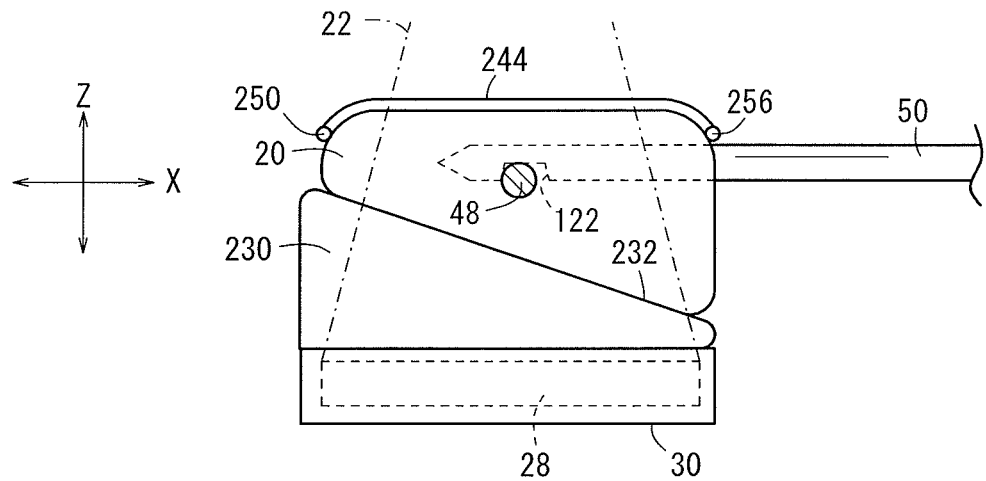
FIGS. 27A and 27B are front elevational views showing the manner in which a biopsy needle is inserted into a breast, which is compressed by a slanted surface of a spacer on an image capturing base and a compression sheet according to a tenth modification.
Figure 27B:
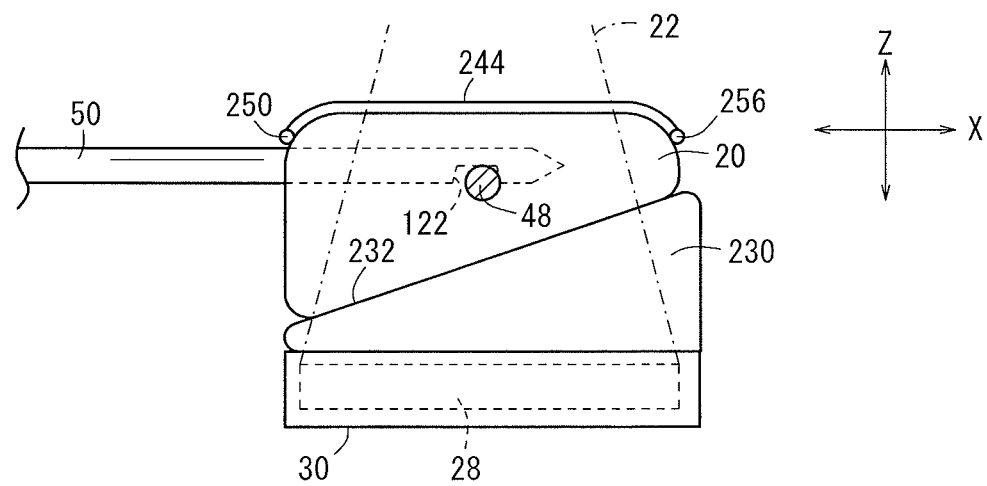

FIGS. 27A and 27B show a tenth modification, which differs from the ninth modification (FIGS. 24 through 26B), in that the breast 20 is compressed and held by the compression sheet 244 according to the ninth modification, together with the spacer 230 according to the eighth modification (FIGS. 23A and 23B).

The spacer 230 has an upper surface 232, which is slanted with respect to the compression sheet 244. The motor-driven cylinders 240, 242 lower the rods 246, 252 the same distance toward the image capturing base 30. The compression sheet 244 covers the upper surface of the breast 20 substantially horizontally along the directions indicated by the arrow X. As a result, the breast 20 is compressed and held under an uneven pressure along the directions indicated by the arrow X, both by the slanted upper surface 232 of the spacer 230 and by the substantially horizontal compression sheet 244. The tenth modification thus offers the same advantages as the eighth and ninth modifications.

Figure 28A:
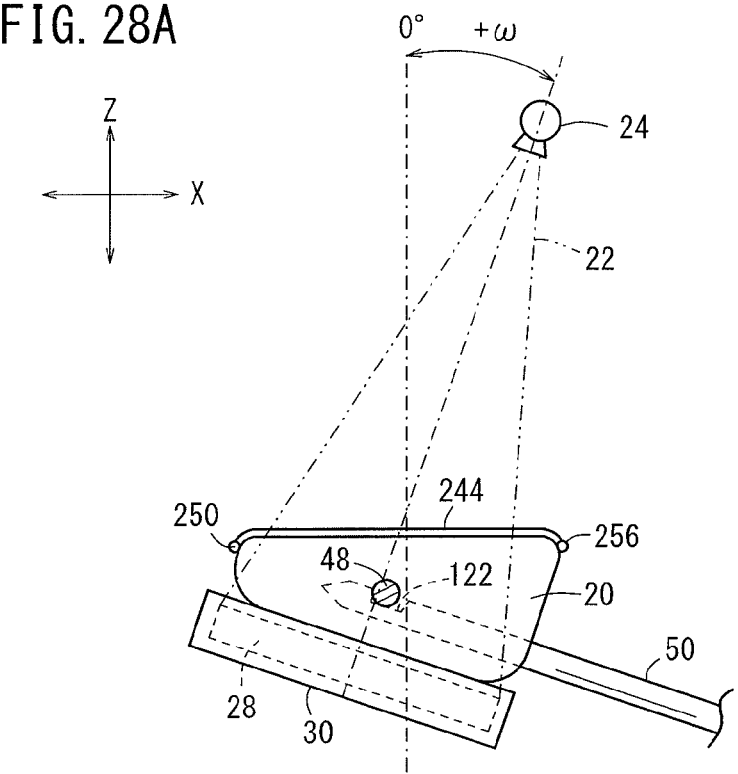
FIGS. 28A and 28B are front elevational views showing the manner in which a biopsy needle is inserted into a breast, which is compressed by a compression sheet and an image capturing base while the image capturing base and a radiation source are turned or tilted with respect to the compression sheet according to an eleventh modification.
Figure 28B:
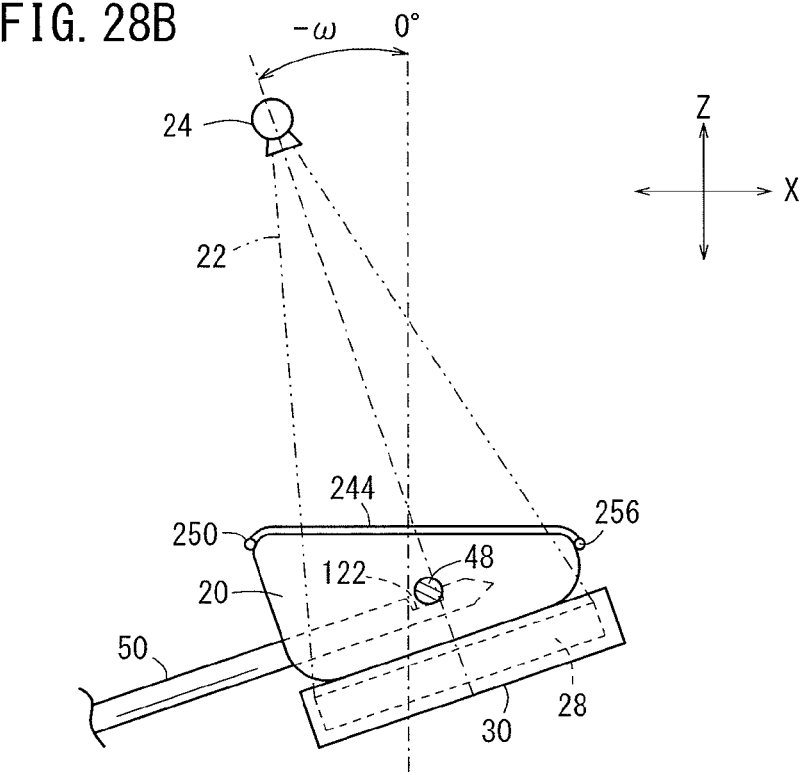

FIGS. 28A and 28B show an eleventh modification, which differs from the ninth and tenth modifications (FIGS. 24 through 27B), in that the arm 16 is turned about the swing shaft 14 according to the sixth modification (FIGS. 21A and 21B), in order to tilt the radiation source housing unit 26 housing the radiation source 24 and the image capturing base 30 with respect to the compression sheet 244.

Upon the arm 16 being turned about the swing shaft 14, the radiation source 24 and the image capturing base 30 are turned through an angle of −ω or +ω. If the motor-driven cylinders 240, 242 lower the rods 246, 252 toward the image capturing base 30, so as to keep the compression sheet 244 substantially horizontal along the directions indicated by the arrow X, the image capturing base 30 is slanted with respect to the substantially horizontal compression sheet 244, thereby compressing and holding the breast 20 under an uneven pressure along the directions indicated by the arrow X. The eleventh modification thus offers the same advantages as the sixth, ninth, and tenth modifications.

In the above embodiment and modifications, the breast 20 of the examinee 18 is compressed and held in position on the image capturing base 30. However, the mammographic apparatus 10 according to the present invention may also be used to compress and hold a phantom, which acts as a target object that simulates the breast 20. The phantom is used for training doctors in carrying out biopsies. The phantom contains a substance that simulates tissue of the biopsy region 48.

Upon the mammographic apparatus 10 compressing and holding the phantom, the mammographic apparatus 10 tilts the compression plate 38 with respect to the image capturing base 30 along lateral directions (i.e., the directions indicated by the arrow X) as viewed in front elevation, and compresses and holds the phantom between the tilted compression plate 38 and the image capturing base 30. Then, according to the lateral approach biopsy procedure, a side region of the phantom is pierced by the biopsy needle 50 to remove the substance as a simulated sample tissue from the phantom.

Although certain preferred embodiments of the present invention have been shown and described in detail, it should be understood that various changes and modifications may be made to the embodiments without departing from the scope of the invention as set forth in the appended claims.

What is claimed is:

1. A radiographic image capturing apparatus comprising:
    a radiation source for applying radiation to a target object to be examined;
    a radiation detector for detecting radiation that has passed through the target object and for converting the detected radiation into a radiographic image;
    a holding member for holding the target object;
    a compression member, configured for displacement toward the holding member for compressing the target object held by the holding member; and
    a tilted direction determiner for determining a tilted direction in which the compression member is tilted with respect to the holding member based on a piercing direction of a sampling needle with respect to the target object when the sampling needle pierces a side region of the target object, which is compressed, along the piercing direction to remove a sample tissue from a test region in the target object,
    wherein the target object is compressed while the compression member is tilted with respect to the holding member along lateral directions of the target object as viewed in front elevation.

2. The radiographic image capturing apparatus according to claim 1, wherein upon the sampling needle piercing the side region of the target object, the tilted direction determiner determines the tilted direction such that the distance between the holding member and the compression member becomes progressively smaller from the side region of the target object toward an opposite side region thereof.

3. The radiographic image capturing apparatus according to claim 1, further comprising:
    a piercing direction determiner for determining the piercing direction of the sampling needle with respect to the target object based on a present position of the sampling needle.

4. The radiographic image capturing apparatus according to claim 1, wherein the compression member comprises a compression plate, which is displaceable from the radiation source toward the holding member, or a compression plate, which is displaceable from the radiation source toward the holding member and a first spacer interposed between the compression plate and the target object, or a compression sheet, which is displaceable from the radiation source toward the holding member; and
    the holding member comprises an image capturing base that houses the radiation detector therein for holding the target object, or an image capturing base that houses the radiation detector therein for holding the target object and a second spacer, which is interposed between the image capturing base and the target object.

5. The radiographic image capturing apparatus according to claim 4, further comprising:
    a compression-plate-side rotational shaft extending in a depth-wise direction of the target object and which is coupled to the compression plate; and
    a rotary actuator for rotating the compression plate about the compression-plate-side rotational shaft, so as to tilt the compression plate with respect to the holding member.

6. The radiographic image capturing apparatus according to claim 4, further comprising:
    a tilted state maintaining mechanism for maintaining the compression plate in a tilted state where the compression plate is tilted, such that an end or an opposite end thereof is closer to the holding member across the target object as viewed in front elevation.

7. The radiographic image capturing apparatus according to claim 5, wherein after the target object has been compressed by the compression plate and the holding member, the compression plate is tilted with respect to the holding member, or alternatively, after the compression plate has been tilted with respect to the holding member, the target object is compressed by the tilted compression plate and the holding member.

8. The radiographic image capturing apparatus according to claim 4, wherein the compression plate has a surface that faces toward the target object and is constructed as a slanted surface, which is inclined with respect to the holding member, wherein the target object is compressed by the holding member and the slanted surface of the compression plate.

9. The radiographic image capturing apparatus according to claim 4, wherein the first spacer has a surface that faces toward the target object and is constructed as a slanted surface, which is inclined with respect to the holding member, wherein the target object is compressed by the holding member and the slanted surface of the first spacer.

10. The radiographic image capturing apparatus according to claim 4, wherein the second spacer has a surface that faces toward the target object and is constructed as a slanted surface, which is inclined with respect to the compression member, wherein the target object is compressed by the compression member and the slanted surface of the second spacer.

11. The radiographic image capturing apparatus according to claim 4, further comprising:
a first rod, which extends in a depth-wise direction of the target object as viewed in front elevation and supports an end of the compression sheet, and a second rod, which extends in the depth-wise direction of the target object and supports an opposite end of the compression sheet;
a first rod movement controller for moving the first rod toward and away from the holding member; and
a second rod movement controller for moving the second rod toward and away from the holding member,
wherein the compression sheet is tilted with respect to the holding member upon the first rod movement controller moving the first rod with respect to the holding member and the second rod movement controller moving the second rod with respect to the holding member.

12. The radiographic image capturing apparatus according to claim 11, wherein the first rod movement controller and the second rod movement controller move the first rod and the second rod to respective different heights above the holding member, for thereby tilting the compression sheet with respect to the holding member.

13. The radiographic image capturing apparatus according to claim 4, further comprising:
a radiation source housing unit housing the radiation source therein;
an arm connecting the radiation source housing unit and the image capturing base to each other;
a compression member support supporting the compression member for movement with respect to the arm; and
an arm-side rotational shaft coupled to the arm,
wherein the arm is turned about the arm-side rotational shaft to tilt the image capturing base with respect to the compression member.

14. A radiographic image capturing apparatus comprising:
a radiation source for applying radiation to a target object to be examined;
a radiation source housing unit housing the radiation source therein;
a radiation detector for detecting radiation that has passed through the target object and for converting the detected radiation into a radiographic image;
an image capturing base housing the radiation detector therein and serving as a holding member for holding the target object;
a compression member, which is capable of being displaced toward the image capturing base for compressing the target object held by the image capturing base;
an arm connecting the radiation source housing unit and the image capturing base to each other;
a compression member support supporting the compression member for movement with respect to the arm; and
an arm-side rotational shaft coupled to the arm,
wherein the arm is turned about the arm-side rotational shaft to tilt the image capturing base with respect to the compression member, and
wherein the target object is compressed while the compression member is tilted with respect to the image capturing base along lateral directions of the target object as viewed in front elevation; and
further comprising a tilted direction determiner for determining a tilted direction in which the compression member is tilted with respect to the image capturing base based on a piercing direction of a sampling needle with respect to the target object when the sampling needle pierces a side region of the target object, which is compressed, along the piercing direction to remove a sample tissue from a test region in the target object.

15. The radiographic image capturing apparatus according to claim 14, wherein the compression member comprises a compression plate, which is displaceable from the radiation source toward the image capturing base, or a compression plate, which is displaceable from the radiation source toward the image capturing base and a first spacer interposed between the compression plate and the target object, or a compression sheet, which is displaceable from the radiation source toward the image capturing base.

\* \* \* \* \*